(12) United States Patent
Gelfand et al.

(10) Patent No.: US 10,150,990 B2
(45) Date of Patent: Dec. 11, 2018

(54) RIBONUCLEOTIDE TAG NUCLEIC ACID DETECTION

(75) Inventors: David H. Gelfand, Oakland, CA (US); Ivo Glynne Gut, Paris (FR); Keith A. Bauer, San Rafael, CA (US); Florence Mauger, Evry (FR)

(73) Assignees: Roche Molecular Systems, Inc., Pleasanton, CA (US); CEA/Institut de Genomique—Centre National de Genotypage, Evry (FR)

( * ) Notice: Subject to any disclaimer, the term of this patent is extended or adjusted under 35 U.S.C. 154(b) by 1685 days.

(21) Appl. No.: 12/421,188

(22) Filed: Apr. 9, 2009

(65) Prior Publication Data

US 2009/0263813 A1    Oct. 22, 2009

Related U.S. Application Data

(60) Provisional application No. 61/046,720, filed on Apr. 21, 2008.

(51) Int. Cl.

| | |
|---|---|
| C12P 1/68 | (2006.01) |
| C12P 19/34 | (2006.01) |
| C12N 9/00 | (2006.01) |
| G01N 31/00 | (2006.01) |
| G01N 33/00 | (2006.01) |
| C07H 21/04 | (2006.01) |
| C07H 21/00 | (2006.01) |
| C12Q 1/6858 | (2018.01) |
| C12Q 1/686 | (2018.01) |

(52) U.S. Cl.
CPC ........... *C12Q 1/6858* (2013.01); *C12Q 1/686* (2013.01)
USPC ............ 435/6.12; 435/91.2; 435/183; 436/2; 436/94; 536/23.1; 536/24.33; 536/25.3; 536/25.6

(58) Field of Classification Search
None
See application file for complete search history.

(56) References Cited

U.S. PATENT DOCUMENTS

| 2004/0241651 A1 | 12/2004 | Olek et al. | |
|---|---|---|---|
| 2006/0141516 A1* | 6/2006 | Kobold et al. | 435/6 |
| 2007/0141593 A1* | 6/2007 | Lee et al. | 435/6 |
| 2007/0269825 A1* | 11/2007 | Wang et al. | 435/6 |

FOREIGN PATENT DOCUMENTS

| CN | 1446928 A | 10/2003 |
|---|---|---|
| EP | 1 173 622 B1 | 11/2000 |
| EP | 1 493 824 A1 | 1/2005 |
| WO | WO 00/66771 A2 | 11/2000 |
| WO | WO 00/66771 A3 | 2/2001 |
| WO | WO 01/77384 A2 | 10/2001 |
| WO | WO 2008/046612 A1 | 4/2008 |
| WO | WO 2009/010251 A2 | 1/2009 |

OTHER PUBLICATIONS

Sommer and Tautz, "Minimal homology requirements for PCR primers," Nucleic Acids Research, 1989, vol. 17, No. 16, p. 6749.*
Sommer and Tautz, "Minimal homology requirements for PCR primers," Nucleic Acids Research, vol. 17, No. 16, 1989, p. 6749.*
"Viruses" (Wikipedia.com, accessed Nov. 24, 2012).*
"How many species of bacteria are there" (wisegeek.com; accessed Jan. 21, 2014).*
"Fungi," (Wikipedia.com; accessed Jun. 3, 2013).*
"Plant," (Wikipedia.com; accessed Mar. 8, 2013).*
"Mammal," (Wikipedia.com; accessed Sep. 22, 2011).*
"Murinae," (Wikipedia.com, accessed Mar. 18, 2013).*
"List of sequenced bacterial genomes" (Wikipedia.com; accessed Jan. 24, 2014).*
"Minimal homology requirements for PCR primers," Nucleic Acids Research, vol. 17, No. 16, 1989, p. 6749.*
Partial European Search Report for EP Application No. 09005451, dated Aug. 7, 2007 (received Aug. 12, 2009); 7 pages.
Mauger et al., "SNP genotyping using alkali cleavage of RNA/DNA chimeras and MALDI time-of-flight mass spectrometry"; *Nucl. Acids. Res.*; 34(3):e18 (8 pages); 2006. XP-002536193.
Sousa, Rui, et al., "A Mutant T7 RNA Polymerase as a DNA Polymerase," *The Embo Journal*, Sep. 15, 1995, vol. 14, No. 18, pp. 4609-4621.

* cited by examiner

*Primary Examiner* — Bradley L. Sisson
(74) *Attorney, Agent, or Firm* — Kilpatrick Townsend & Stockton LLP

(57) ABSTRACT

The present application provides polynucleotides comprising 5'-tails with sequence segments useful for the detection of target nucleic acid sequences, and methods for their use in detecting target nucleic acids. The polynucleotides are used to amplify a subsequence of a target nucleic acid in the presence of one or more ribonucleotides. The ribonucleotides are incorporated into amplification products at regular intervals complementary to the 5'-tail sequence segments. Cleavage of amplification products at the bond immediately 3' to incorporated ribonucleotides produces detectably distinct fragments indicative of the presence or absence of a target nucleic acid.

12 Claims, 11 Drawing Sheets

Specification includes a Sequence Listing.

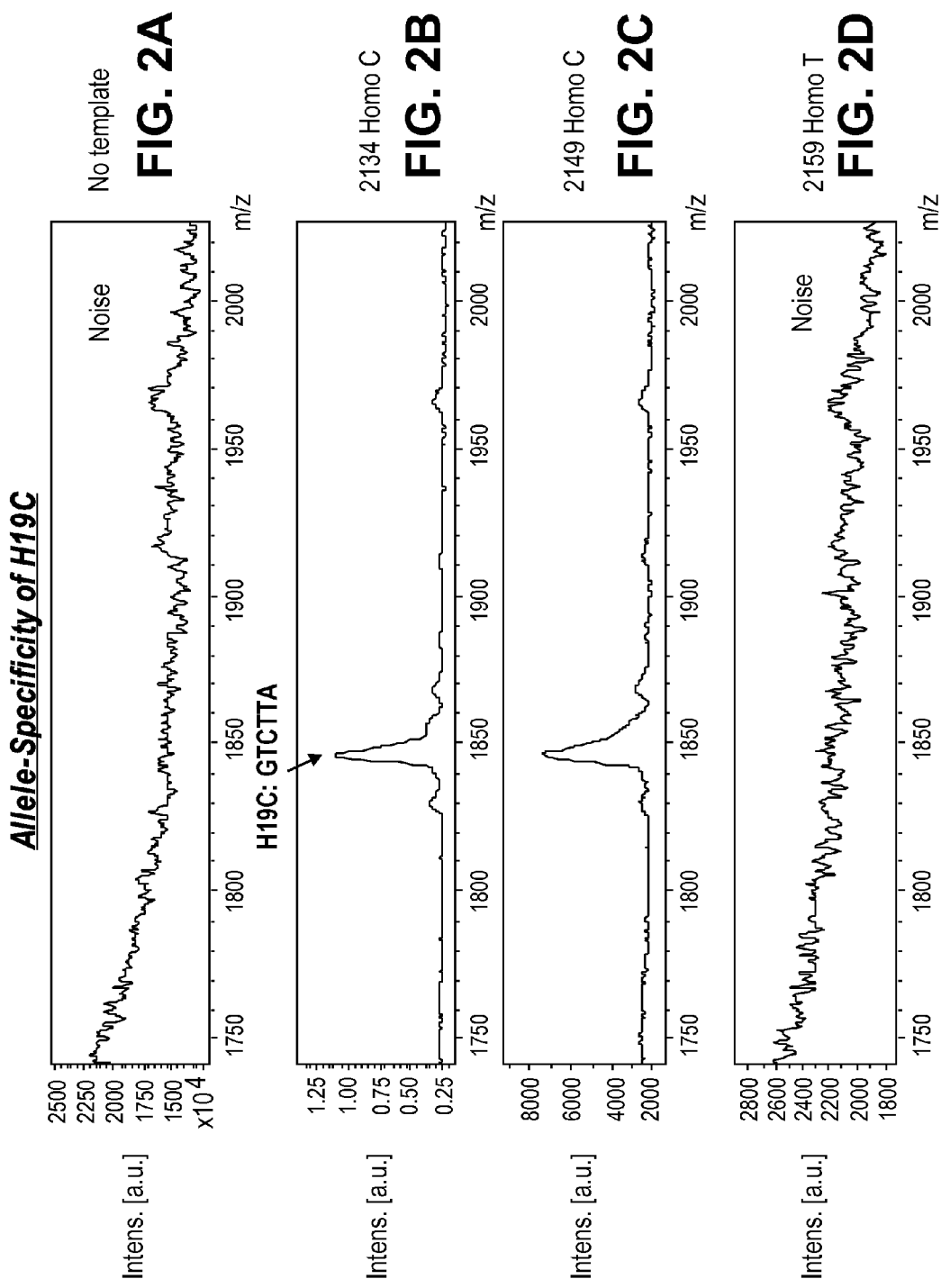

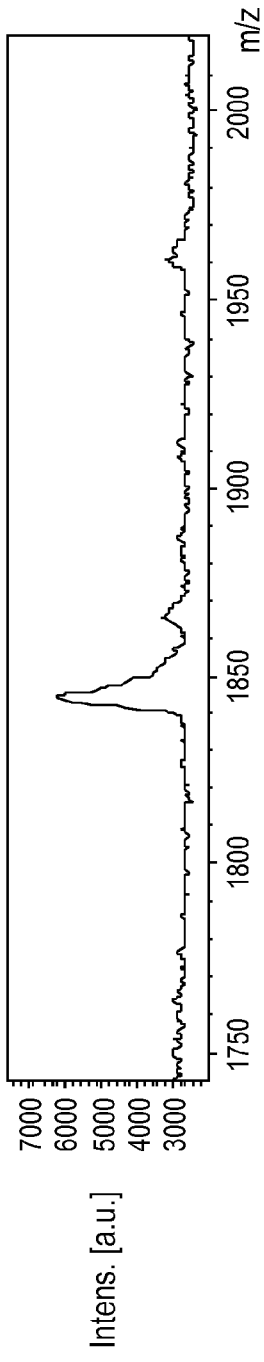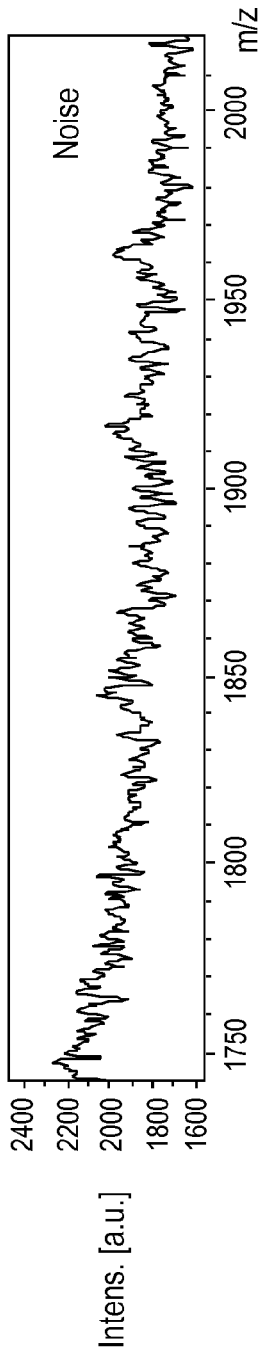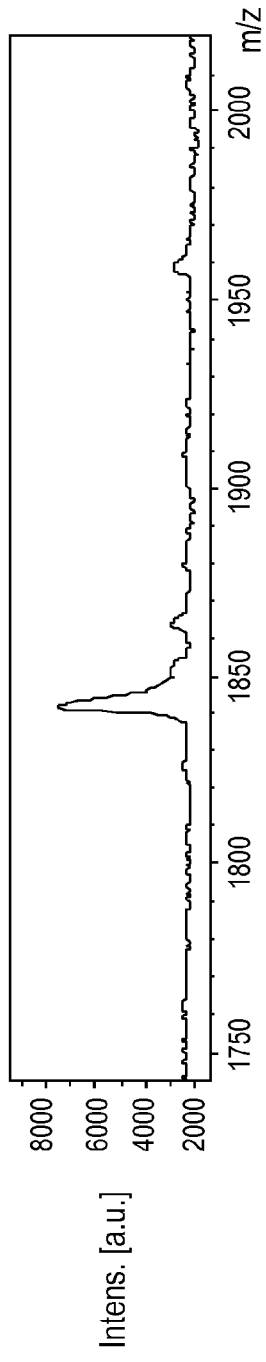

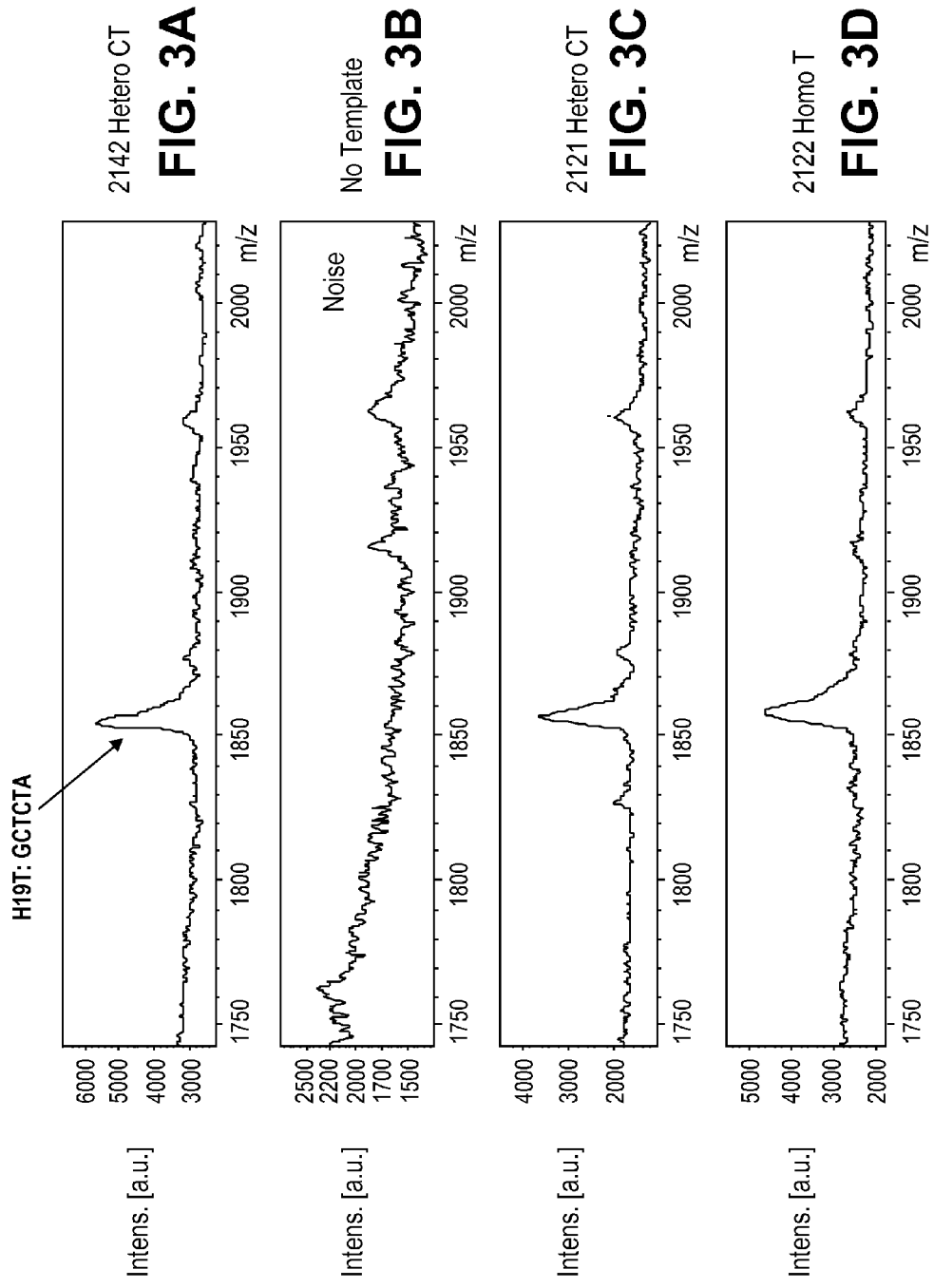

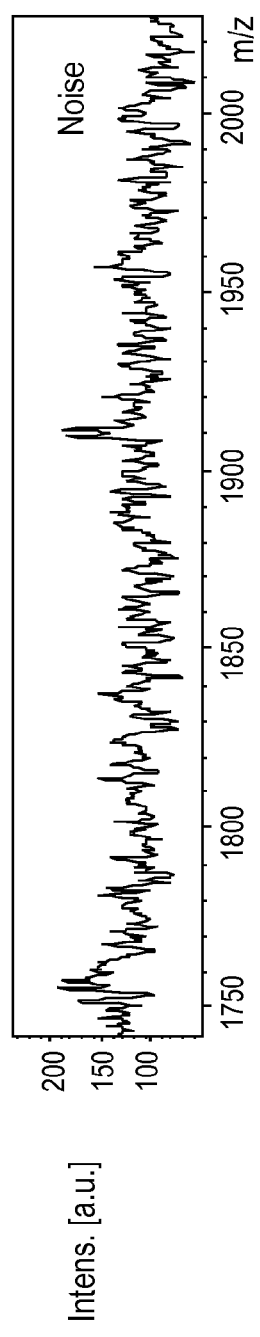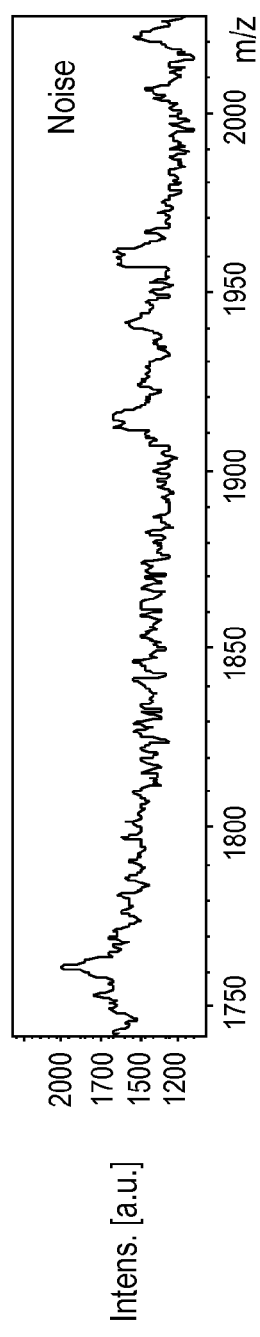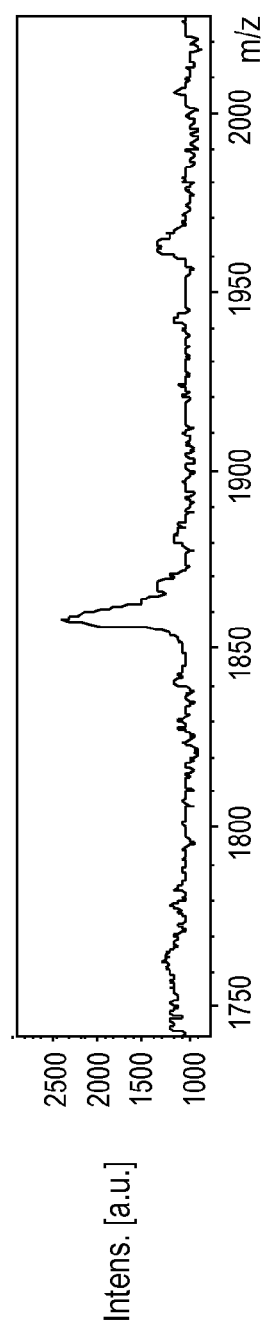

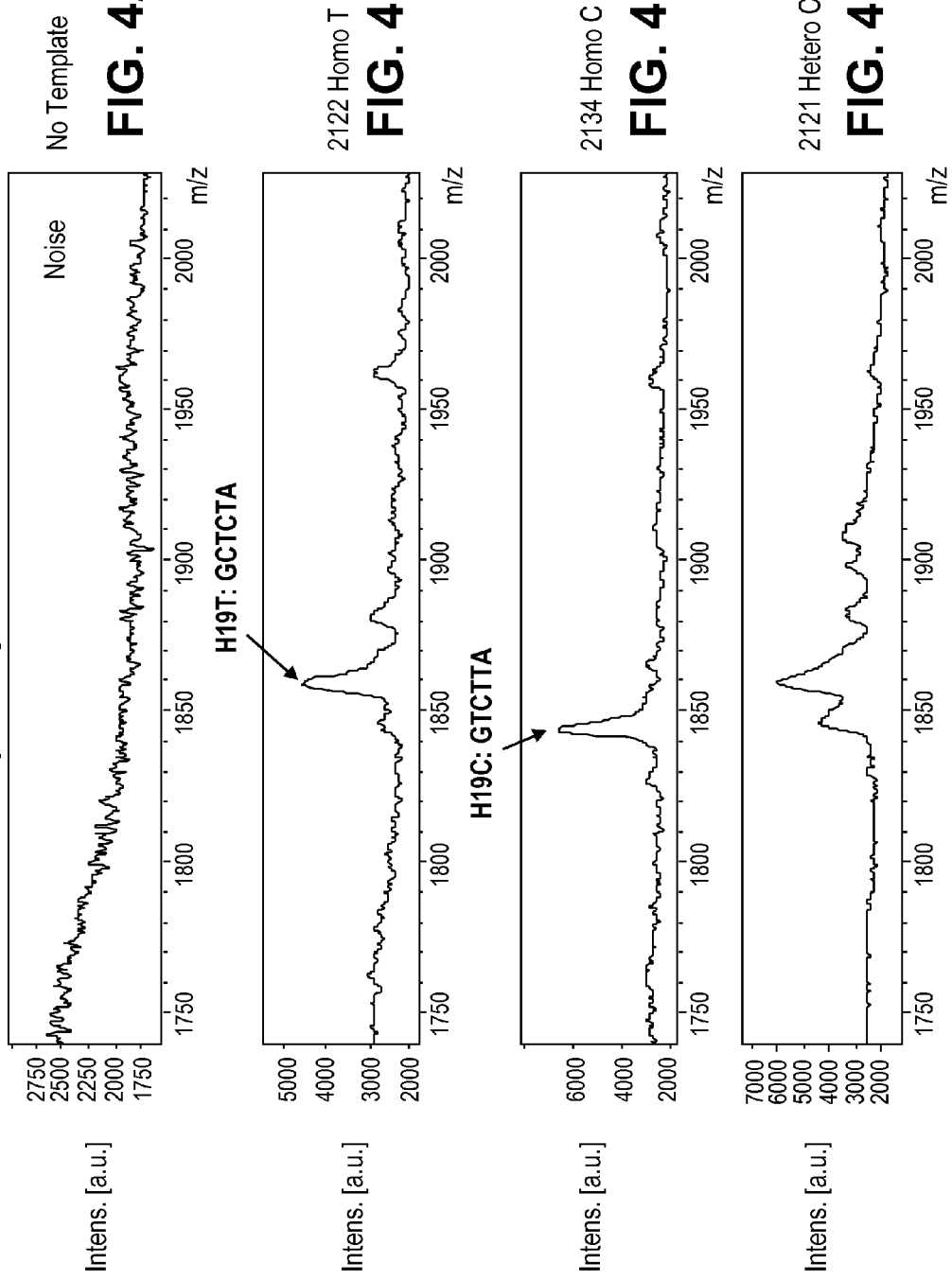

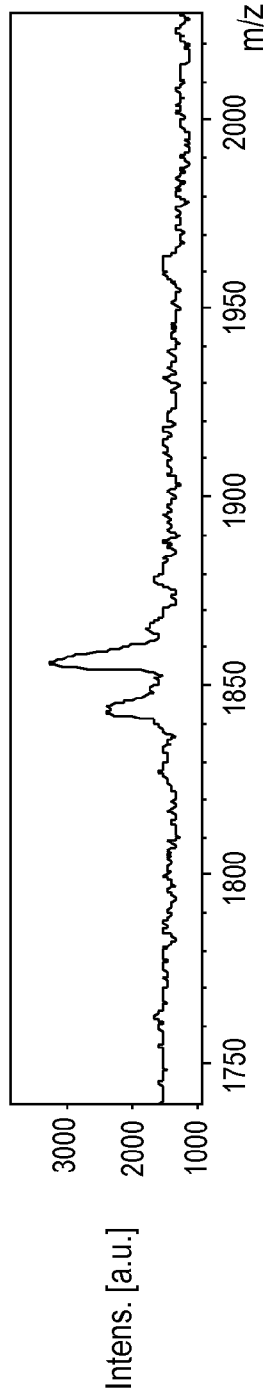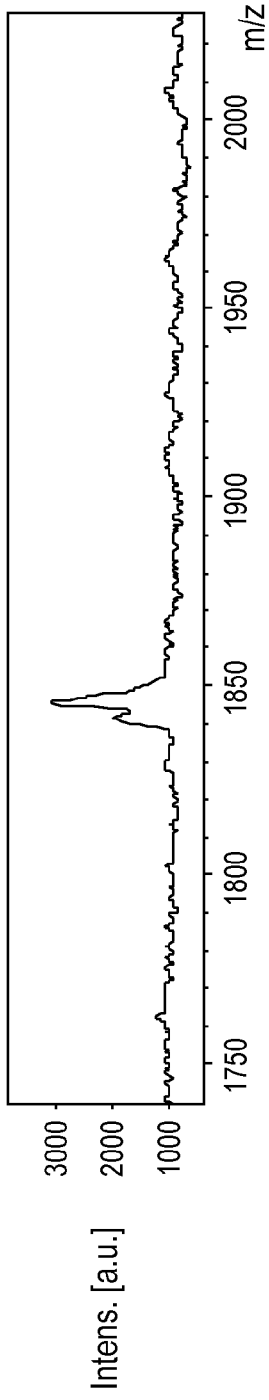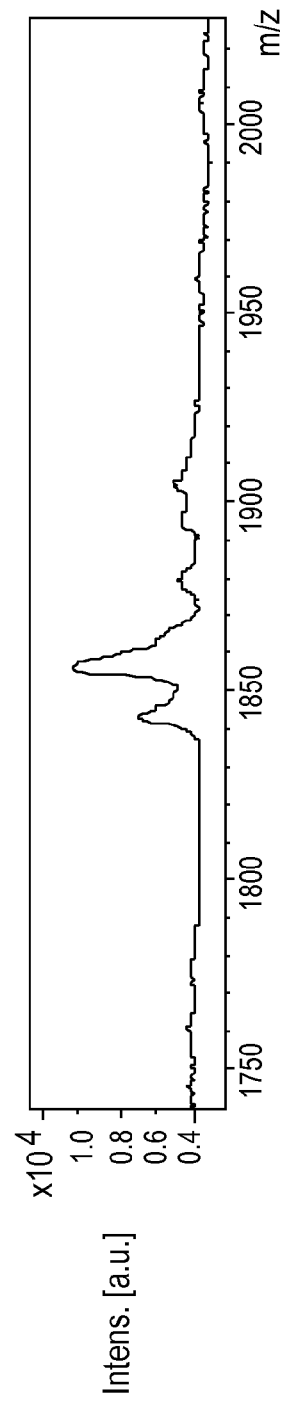

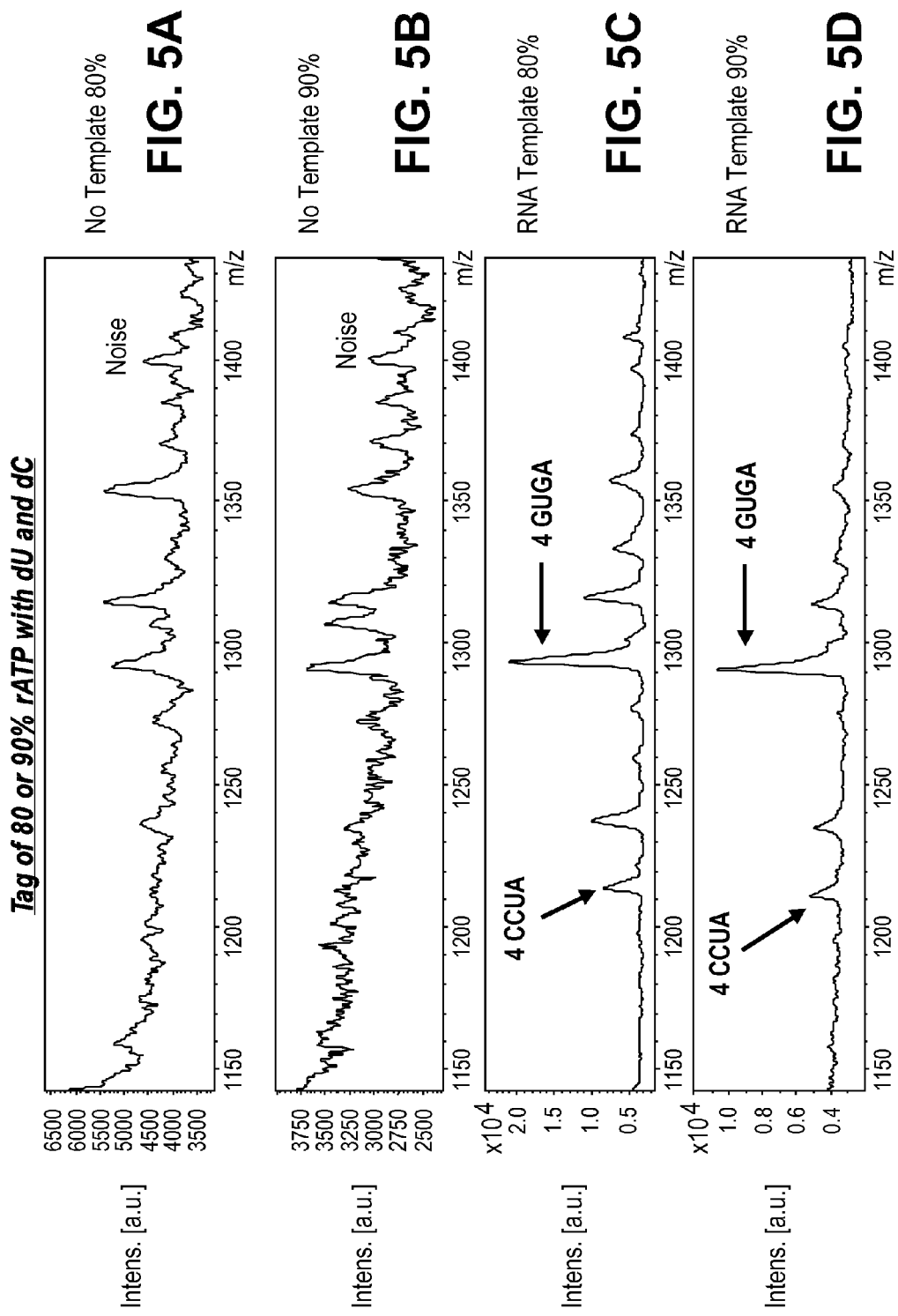

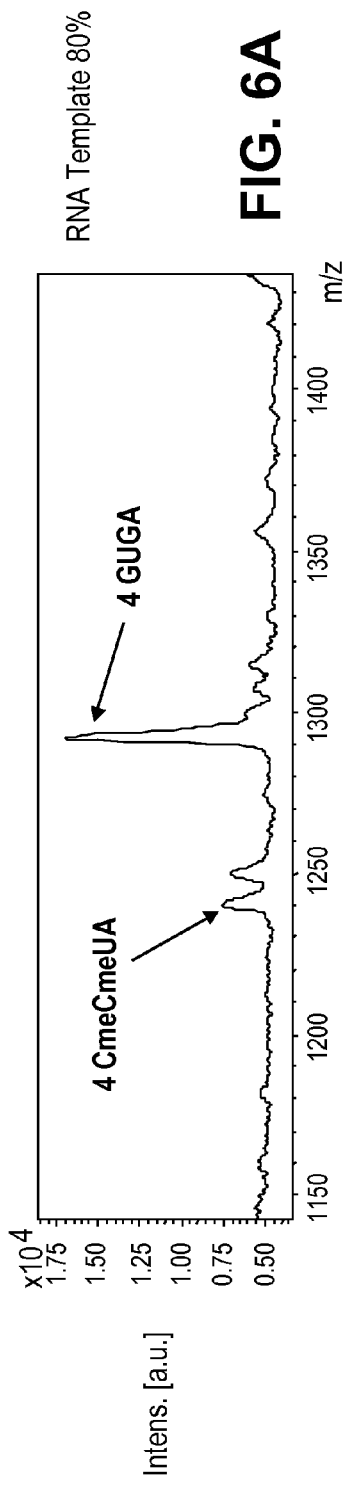
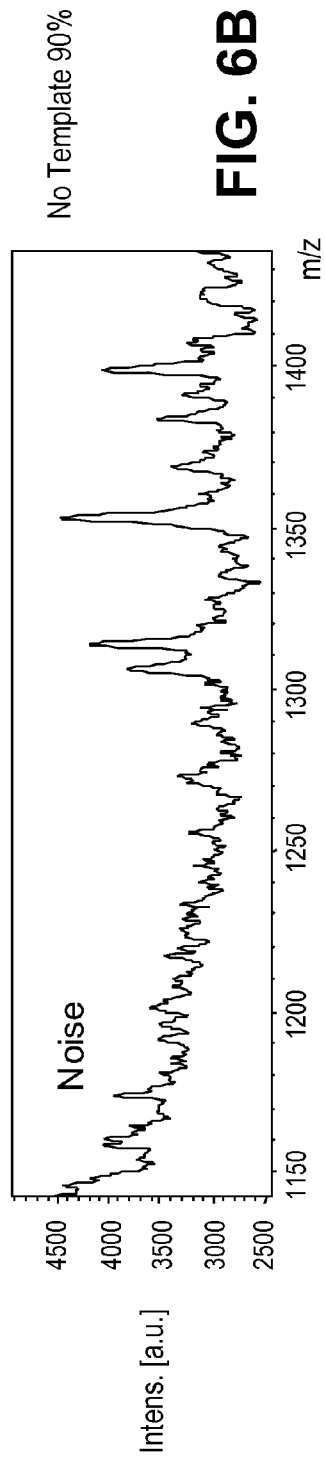
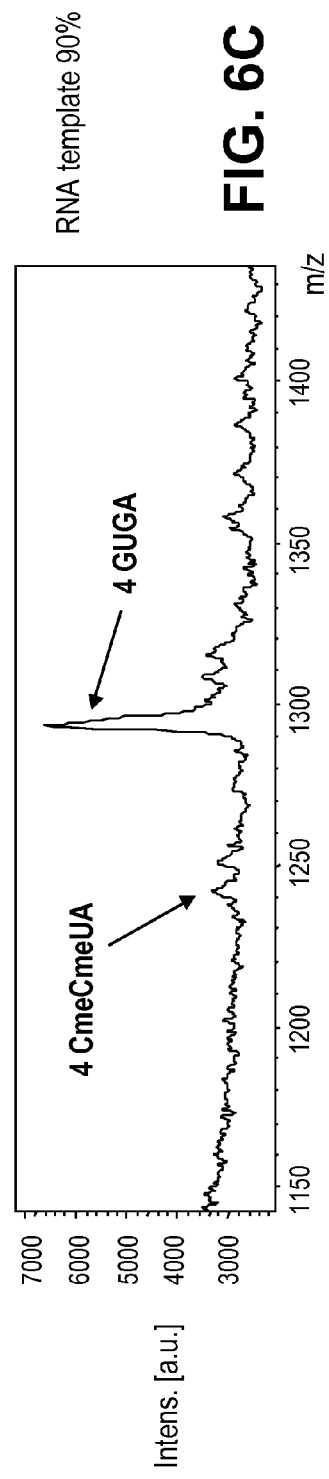
FIG. 6A
FIG. 6B
FIG. 6C

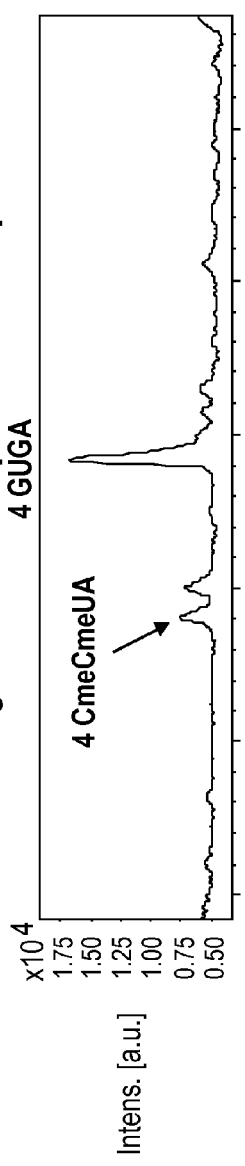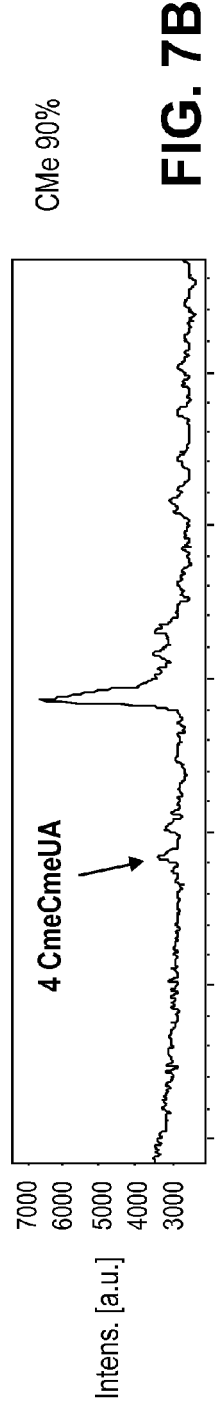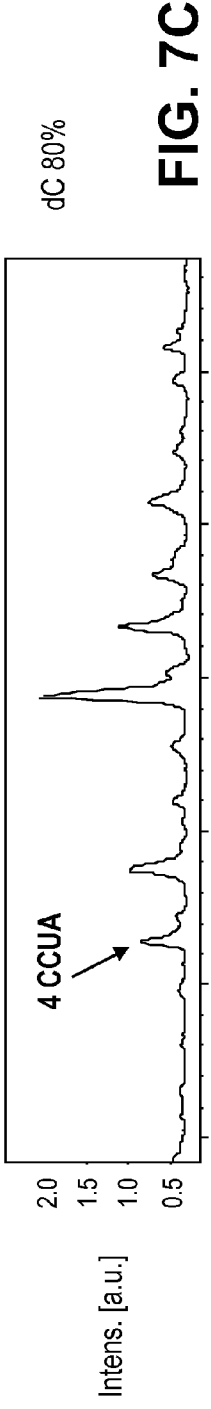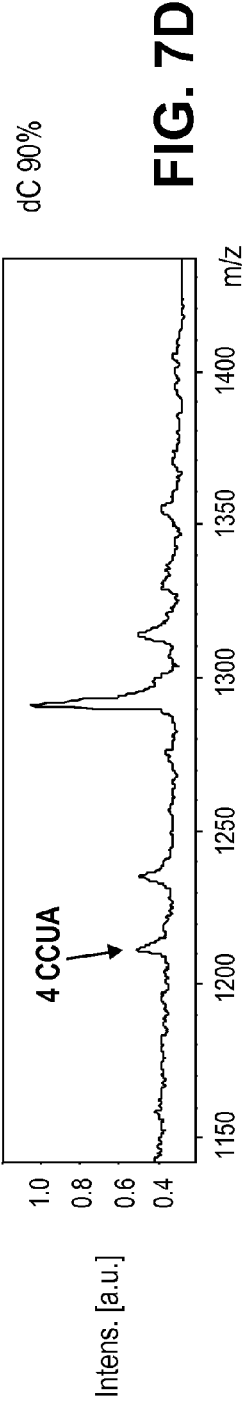
FIG. 7A
FIG. 7B
FIG. 7C
FIG. 7D

RIBONUCLEOTIDE TAG NUCLEIC ACID DETECTION

CROSS-REFERENCE TO RELATED APPLICATIONS

This application claims the benefit of U.S. Provisional Application No. 61/046,720, filed on Apr. 21, 2008, the entire disclosure of which is hereby incorporated herein by reference.

FIELD OF THE INVENTION

The present invention relates to the field of nucleic acid detection. In particular, the present invention provides polynucleotides having multiple contiguous sequence segments, wherein the 5'-end nucleotide base of each sequence segment is unique within the sequence segment and is the same in each sequence segment, and methods for their use in detecting target nucleic acids.

BACKGROUND OF THE INVENTION

Many methods for detection of target nucleic acids (e.g., SNP genotyping) are known. Currently available homogeneous assays for SNP genotyping include the TAQMAN®, AMPLIFLUOR®, dye binding, allele-selective kinetic PCR, and SCORPION® primer assays. These assays provide one, or at maximum two (if using four different fluorescent dyes) SNPs per reaction well (e.g. dye-binding kinetic PCR requires two wells for one SNP). The available methods for SNP genotyping range from those that allow genotyping of a single SNP in a reaction well to methods that permit genotyping of many thousand SNPs in a single well (e.g., GOLDEN GATE® Assay, Illumina). Present genotyping assay procedures are not readily multiplexed due to the requirement for a different dye for each typed allele, and thus is limited in its potential for improvement. The GOLDEN GATE® assay requires complex analysis devices such as fiber optic array readers. Analyzers for reading of SNP genotyping range from plate readers (optionally, with an included PCR machine), to sequencers (e.g., capillary sequencers), array readers and mass spectrometers. Moreover, to the extent that mass spectrometers have been used for genotyping, currently available procedures do not allow for true multiplexing.

BRIEF SUMMARY OF THE INVENTION

The present invention provides polynucleotides for the efficient and highly sensitive concurrent detection of one or more target nucleic acids. The polynucleotides are designed with a 5'-portion comprising one, two or more contiguous sequence segments, such that the mass of a sequence segment, or complement thereof, identifies a target nucleic acid or a target nucleotide within a target nucleic acid. In some embodiments, the sequence segments are of equal mass. Sequence segments of equal mass can, but need not have the same sequence. The sequence segments are cleaved from the complement of the polynucleotide and their mass is measured or detected to identify the presence, absence or level of presence of a target nucleic acid.

Accordingly, in a first aspect, the present invention provides a polynucleotide comprising one, two or more sequence segments. In some embodiments, the polynucleotide comprises a 5' portion and a 3' portion, wherein a) the 5' portion comprises at least one or at least two contiguous sequence segments, wherein each sequence segment comprises at least three nucleotide bases, is of equal mass, and the 5'-end nucleotide base of each sequence segment is unique within one sequence segment and is the same in each sequence segment; and b) the 3' portion comprises at least 5 nucleotides, wherein the polynucleotide is less than about 100 nucleotide bases in length. In some embodiments, the polynucleotide is less than about 75, 50 or 25 nucleotides in length.

In some embodiments, each sequence segment has the same nucleotide sequence.

In some embodiments, the 5' portion comprises at least 3, 4, 5, 6, 7 or 8 contiguous sequence segments. In some embodiments, each sequence segment comprises at least 3, 4, 5, 6, 7 or 8 nucleotides.

In some embodiments, the 3'-end comprises a removable blocking moiety that substantially prevents extension of the polynucleotide. In some embodiments, the 3'-end comprises a 2' terminator moiety.

In a further aspect, the invention provides methods of detecting a target nucleic acid. In some embodiments, the methods comprise:

(a) contacting the target nucleic acid with a polynucleotide, a nucleotide set and a nucleotide incorporating biocatalytic component, wherein;
  (i) the polynucleotide comprises a 5' portion and a 3' portion, the 5' portion comprising at least one or at least two contiguous sequence segments, wherein each sequence segment comprises at least three nucleotide bases, and the 5'-end nucleotide base of each sequence segment is unique within one sequence segment and is the same in each sequence segment; and the 3' portion comprising a sequence segment that is substantially complementary sufficient to hybridize to the target nucleic acid and be extended under amplification conditions;
  (ii) the nucleotide set comprises at least two nucleotide bases in the form of deoxyribonucleotides (dNTPs), and the majority of at least one nucleotide base in the form of a ribonucleotide (rNTP), wherein the base of the ribonucleotide is complementary to the unique 5' nucleotide base of each sequence segment of the polynucleotide; and
  (iii) the nucleotide incorporating biocatalytic component comprises deoxyribonucleotide and ribonucleotide incorporating activities;

(b) amplifying the target nucleic acid under amplification conditions to produce an amplicon comprising a 3' sequence segment (i.e., 3'-portion) complementary to the 5'-portion of the polynucleotide, wherein the 3' sequence segment comprises at least one or at least two sequence segments, wherein the 3' end nucleotide base of each sequence segment is a nucleoside monophosphate (NMP) having the same base as the NTP in the nucleotide set;

(c) cleaving the amplicon 3' of each NMP into fragments, wherein the cleaving releases the sequence segments as individual fragments; and (d) detecting the amplicon fragments, wherein the detected sequence segment fragments indicate amplification of the target nucleic acid sequence, thereby detecting the target nucleic acid sequence.

In some embodiments, the 5' portion sequence segments are of equal mass.

In some embodiments, at least 80% of at least one nucleotide base is in the form of a ribonucleotide (rNTP).

In some embodiments, the cleaving is performed by subjecting the amplicon to an alkaline solution.

In some embodiments, the alkaline solution comprises at least one of the following: NaOH, KOH, RbOH, $Mg(OH)_2$, $Ca(OH)_2$, or $NH_4OH$. In some embodiments, the alkaline solution comprises at least one of the following: NaOH, KOH or $NH_4OH$.

In some embodiments, the methods further comprise the step of contacting the target nucleic acid sequence with a polynucleotide pair, wherein each polynucleotide in the polynucleotide pair comprise 5' portion sequence segments of equal mass.

In some embodiments, the methods further comprise the step of contacting the target nucleic acid with at least one polynucleotide, wherein the detection of the sequence segment fragments from the polynucleotide, or its complement, indicates the presence of an allele of a polymorphic nucleotide in the target nucleic acid sequence.

In some embodiments, the methods further comprise the step of contacting the target nucleic acid with at least two different polynucleotides, wherein the polynucleotides differ only at the 3'-end nucleotide base, wherein the 3'-end nucleotide base of each polynucleotide corresponds to a sequence segment of unique mass, and the detection of the sequence segment fragments from at least one of the polynucleotides, or its complement, indicates the presence of an allele of a polymorphic nucleotide in the target nucleic acid sequence.

In some embodiments, a plurality of different target nucleic acid sequences is contacted with a plurality of different polynucleotides, each of the different polynucleotides comprising sequence segments of a unique mass, wherein the sequence segments of the polynucleotides are identifiers of one of the plurality of different target nucleic acid sequences, whereby detection of the sequence segment fragments from at least one of the polynucleotides, or its complement, indicates the presence of at least one of the plurality of different target nucleic acid sequences.

In some embodiments, the nucleotide incorporating biocatalytic component comprises a single catalytic domain that comprises deoxyribonucleotide and ribonucleotide incorporating activities. In some embodiments, the nucleotide incorporating biocatalytic component comprises first and second catalytic domains, wherein the first catalytic domain comprises deoxyribonucleotide incorporating activity and the second catalytic domain comprises ribonucleotide incorporating activity.

In some embodiments, the detecting is performed by mass spectrometry. In some embodiments, the detection is by gas-phase ion mass spectrometry. In some embodiments, the detection is by laser desorption-ionization mass spectrometry.

In some embodiments, the polynucleotide comprises a blocking moiety that substantially prevents extension of the polynucleotide, and wherein the method further comprises the step of removing the blocking moiety from the polynucleotide prior to amplifying.

In another aspect, the invention provides reaction mixtures. In some embodiments, the reaction mixtures comprise:

a) a first polynucleotide comprising a 5' portion and a 3' portion, wherein the 5' portion comprises at least one or at least two contiguous sequence segments, wherein each sequence segment comprises at least three nucleotide bases, and the 5'-end nucleotide base of each sequence segment is unique within one sequence segment and is the same in each sequence segment; and the 3' portion comprises a sequence segment that is substantially complementary sufficient to hybridize to a target nucleic acid and be extended under amplification conditions;

b) a nucleotide set comprising at least two nucleotide bases in the form of deoxyribonucleotides (dNTPs), and the majority of at least one nucleotide base in the form of a ribonucleotide (rNTP), wherein the nucleotide base provided as a ribonucleotide is complementary to the unique 5' nucleotide base of each sequence segment; and c) a nucleotide incorporating biocatalytic component comprising deoxyribonucleotide and ribonucleotide incorporating activities.

In a related aspect, the invention provides kits. In some embodiments, the kits comprise:

a) a first polynucleotide comprising a 5' portion and a 3' portion, wherein the 5' portion comprises at least one or at least two contiguous sequence segments, wherein each sequence segment comprises at least three nucleotide bases, and the 5'-end nucleotide base of each sequence segment is unique within one sequence segment and is the same in each sequence segment; and the 3' portion comprises a sequence segment that is substantially complementary sufficient to hybridize to a target nucleic acid and be extended under amplification conditions;

b) a nucleotide set comprising at least two nucleotide bases in the form of deoxyribonucleotides (dNTPs), and the substantial majority of at least one nucleotide base in the form of a ribonucleotide (rNTP), wherein the nucleotide base provided as a ribonucleotide is complementary to the unique 5' nucleotide base of each sequence segment; and c) a nucleotide incorporating biocatalytic component comprising deoxyribonucleotide and ribonucleotide incorporating activities.

Embodiments of the reaction mixtures and kits are as described above for the polynucleotides and the methods, and herein.

In a further aspect, the invention provides amplicons. In some embodiments, the amplicons comprise a double-stranded polynucleotide comprising:

a) a first strand comprising a 5' portion and a 3' portion, wherein the 5' portion comprises at least one or at least two contiguous sequence segments, wherein each sequence segment comprises at least three nucleotide bases, is of equal mass, and the 5'-end nucleotide base of each sequence segment is unique within one sequence segment and is the same in each sequence segment; and the 3' portion comprises at least 5 nucleotides; and b) a second strand complementary to the first strand and comprising a 3' portion comprising a sequence segment comprising at least one or at least two contiguous sequence segments, wherein the 3'-end nucleotide base of each sequence segment is an NMP.

In another aspect, the invention provides systems. In some embodiments, the systems comprise at least one container or support comprising:

a) a composition comprising an amplicon of the invention;

b) at least one thermal modulator configured to thermally communicate with the container or the support to modulate temperature in the container or on the support;

c) at least one reagent transfer component that transfers reagents to and/or from the container or the support; and, d) at least one detector configured to detect masses of one or more sequence segments produced in the container or on the support.

In some embodiments, the detector comprises a gas-phase ion spectrometer.

In some embodiments, the systems comprise at least one controller operably connected to:

the thermal modulator to effect modulation of the temperature in the container or on the support, the reagent transfer component to effect transfer of the reagents to and/or from the container or on the support, and/or, the detector to effect detection of the masses of the sequence segments produced in the container or on the support.

DEFINITIONS

The terms "nucleic acid" or "polynucleotide" apply interchangeably to a polymer that corresponds to a ribose nucleic acid (RNA) or deoxyribose nucleic acid (DNA) polymer, or an analog thereof. This includes polymers of nucleotides such as RNA and DNA, as well as modified forms thereof, peptide nucleic acids (PNAs), locked nucleic acids (LNA™), and the like. In certain embodiments, a nucleic acid can be a polymer that includes multiple monomer types, e.g., both RNA and DNA subunits. A nucleic acid can be or can include, e.g., a chromosome or chromosomal segment, a vector (e.g., an expression vector), an expression cassette, a naked DNA or RNA polymer, the product of a polymerase chain reaction (PCR), an oligonucleotide, a probe, a primer, etc. A nucleic acid can be, e.g., single-stranded, double-stranded, triple-stranded, etc and is not limited to any particular length. Unless otherwise indicated, a particular nucleic acid sequence optionally comprises or encodes complementary sequences, in addition to any sequence explicitly indicated.

Nucleic acids are not limited to molecules having naturally occurring polynucleotide sequences or structures, naturally occurring backbones, and/or naturally occurring internucleotide linkages. For example, nucleic acids containing one or more carbocyclic sugars are also included within this definition (Jenkins et al. (1995) *Chem. Soc. Rev.* pp 169-176, which is incorporated by reference). To further illustrate, although a nucleic acid will generally contain phosphodiester bonds, in some cases nucleic acid analogs are included that have alternate backbones. These include, without limitation, phosphoramide (Beaucage et al. (1993) *Tetrahedron* 49(10): 1925 and the references therein; Letsinger (1970) *J. Org. Chem.* 35:3800; Sprinzl et al. (1977) *Eur. J. Biochem.* 81:579; Letsinger et al. (1986) *Nucl. Acids Res.* 14: 3487; Sawai et al. (1984) *Chem. Lett.* 805; Letsinger et al. (1988) *J. Am. Chem. Soc.* 110:4470; and Pauwels et al. (1986) *Chemica Scripta* 26:1419), phosphorothioate (Mag et al. (1991) *Nucleic Acids Res.* 19:1437 and U.S. Pat. No. 5,644, 048), phosphorodithioate (Briu et al. (1989) *J. Am. Chem. Soc.* 111:2321), O-methylphosphoroamidite linkages (Eckstein, *Oligonucleotides and Analogues: A Practical Approach*, Oxford University Press (1992)), and peptide nucleic acid backbones and linkages (Egholm (1992) *J. Am. Chem. Soc.* 114:1895; Meier et al. (1992) *Chem. Int. Ed. Engl.* 31:1008; Nielsen (1993) *Nature* 365:566; and Carlsson et al. (1996) *Nature* 380:207), which references are each incorporated by reference.

Other analog nucleic acids include those with positively charged backbones (Denpcy et al. (1995) *Proc. Natl. Acad. Sci. USA* 92:6097); non-ionic backbones (U.S. Pat. Nos. 5,386,023, 5,637,684, 5,602,240, 5,216,141 and 4,469,863; Angew (1991) Chem. Intl. Ed. English 30: 423; Letsinger et al. (1988) *J. Am. Chem. Soc.* 110:4470; Letsinger et al. (1994) *Nucleoside & Nucleotide* 13:1597; Chapters 2 and 3, ASC Symposium Series 580, "Carbohydrate Modifications in Antisense Research", Ed. Y. S. Sanghvi and P. Dan Cook; Mesmaeker et al. (1994) *Bioorganic & Medicinal Chem. Lett.* 4: 395; Jeffs et al. (1994) *J. Biomolecular NMR* 34:17; *Tetrahedron Lett.* 37:743 (1996)) and non-ribose backbones, including those described in U.S. Pat. Nos. 5,235,033 and 5,034,506, and Chapters 6 and 7, ASC Symposium Series 580, *Carbohydrate Modifications in Antisense Research*, Ed. Y. S. Sanghvi and P. Dan Cook, which are each incorporated by reference. Several nucleic acid analogs are also described in, e.g., Rawls, C & E News Jun. 2, 1997 page 35, which is incorporated by reference. Modifications of the ribose-phosphate backbone may be done to facilitate the addition of additional moieties, such as labeling moieties, or to alter the stability and half-life of such molecules in physiological environments.

In addition to naturally occurring heterocyclic bases that are typically found in nucleic acids (e.g., adenine, guanine, thymine, cytosine, and uracil), nucleic acid analogs also include those having non-naturally occurring heterocyclic or other modified bases. To illustrate, certain bases used in nucleotides that act as melting temperature ($T_m$) modifiers are optionally included. For example, some of these include 7-deazapurines (e.g., 7-deazaguanine, 7-deazaadenine, etc.), pyrazolo[3,4-d]pyrimidines, propynyl-dN (e.g., propynyl-dU, propynyl-dC, etc.), and the like. See, e.g., U.S. Pat. No. 5,990,303, which is incorporated by reference. Other representative heterocyclic bases include, e.g., hypoxanthine, inosine, xanthine; 8-aza derivatives of 2-aminopurine, 2,6-diaminopurine, 2-amino-6-chloropurine, hypoxanthine, inosine and xanthine; 7-deaza-8-aza derivatives of adenine, guanine, 2-aminopurine, 2,6-diaminopurine, 2-amino-6-chloropurine, hypoxanthine, inosine and xanthine; 6-azacytosine; 5-fluorocytosine; 5-chlorocytosine; 5-iodocytosine; 5-bromocytosine; 5-methylcytosine; 5-propynylcytosine; 5-bromovinyluracil; 5-fluorouracil; 5-chlorouracil; 5-iodouracil; 5-bromouracil; 5-trifluoromethyluracil; 5-methoxymethyluracil; 5-ethynyluracil; 5-propynyluracil, and the like. Many non-naturally occurring bases are also described in, e.g., Seela et al. (1991) *Helv. Chim. Acta* 74:1790, Grein et al. (1994) *Bioorg. Med. Chem. Lett.* 4:971-976, and Seela et al. (1999) *Helv. Chim. Acta* 82:1640, which are each incorporated by reference. Additional examples of modified bases and nucleotides are also described in, e.g., U.S. Pat. Nos. 5,484,908; 5,645,985; 5,830,653; 6,639,059; 6,303,315; and U.S. Pat. Application Pub. No. 2003/0092905, which are each incorporated by reference.

A "nucleotide" refers to an ester of a nucleoside, e.g., a phosphate ester of a nucleoside. To illustrate, a nucleotide can include 1, 2, 3, or more phosphate groups covalently linked to a sugar moiety of the nucleoside (e.g., at a 5' position, 3' position, 2' position, etc.).

A "nucleotide incorporating biocatalyst" refers to a catalyst that catalyzes the incorporation of nucleotides into a nucleic acid. Nucleotide incorporating biocatalysts are typically enzymes. An "enzyme" is a protein-based catalyst that acts to reduce the activation energy of a chemical reaction involving other compounds or "substrates." A "nucleotide incorporating enzyme" refers to an enzyme that catalyzes the incorporation of nucleotides into a nucleic acid. Exemplary nucleotide incorporating enzymes include, e.g., DNA polymerases, RNA polymerases, terminal transferases, reverse transcriptases, telomerases, polynucleotide phosphorylases, and the like. Other biocatalysts may be DNA-based ("DNAzymes") or RNA-based ("ribozymes"). A "thermostable enzyme" refers to an enzyme that is stable to heat, is heat resistant and retains sufficient catalytic activity when subjected to elevated temperatures for selected periods of time. For example, a thermostable polymerase retains sufficient activity to effect subsequent primer extension reactions when subjected to elevated temperatures for the time necessary to effect denaturation of double-stranded nucleic acids. Heating conditions necessary for nucleic acid denaturation are well known in the art and are exemplified in U.S. Pat. No. 4,683,202, entitled "PROCESS FOR AMPLIFYING NUCLEIC ACID SEQUENCES," issued Jul. 28, 1987 to Mullis and U.S. Pat. No. 4,683,195, entitled "PROCESS FOR AMPLIFYING, DETECTING, AND/OR-CLONING NUCLEIC ACID SEQUENCES," issued Jul. 28, 1987 to Mullis et al., which are both incorporated by reference. As used herein, a thermostable polymerase is typically suitable for use in a temperature cycling reaction such as a PCR or a 5'-nuclease reaction. For a thermostable polymerase, enzymatic activity refers to the catalysis of the polymerization of the nucleotides in the proper manner to form primer extension products that are complementary to a template nucleic acid.

Exemplary nucleotide incorporating biocatalysts include, e.g., a G46E E678G CS5 DNA polymerase, a G46E L329A E678G CS5 DNA polymerase, a G46E L329A D640G S671F CS5 DNA polymerase, a G46E L329A D640G S671F E678G CS5 DNA polymerase, a G46E E678G CS6 DNA polymerase, a ΔZ05R polymerase, a E615G Taq DNA polymerase, a *Thermus flavus* polymerase, a TMA-25 polymerase, a E678G TMA-25 polymerase, a TMA-30 polymerase, a E678G TMA-30 polymerase, a Tth DNA polymerase, a *Thermus* specie SPS-17 polymerase, a E615G Taq polymerase, a *Thermus* Z05R polymerase, a T7 DNA polymerase, a Kornberg DNA polymerase I, a Klenow DNA polymerase, a Taq DNA polymerase, a Micrococcal DNA polymerase, an alpha DNA polymerase, a reverse transcriptase, an AMV reverse transcriptase, an M-MuLV reverse transcriptase, a DNA polymerase, an RNA polymerase, an *E. coli* RNA polymerase, an SP6 RNA polymerase, a T3 RNA polymerase, a T4 DNA polymerase, a T7 RNA polymerase, an RNA polymerase II, a terminal transferase, a polynucleotide phosphorylase, a ribonucleotide incorporating DNA polymerase, and the like.

The term "sequence segment" refers to a polynucleotide subsequence of the 5'-portion (i.e., 5'-tail) of the polynucleotides of the invention. The 5'-portions contain one, two or more sequence segments, each sequence segment having a unique base positioned at the 5'-end that is the same for all sequence segments in a 5'-tail of one polynucleotide. The sequence segments can have from about 3-10 or more bases in length, for example, about 3-8, 3-6, 4-6, 4-8 or 7-8 bases in length, and a 5'-portion can contain from 2 to about 10 or more sequence segments. The sequence segments can, but need not be of equal mass. Sequence segments of equal mass can, but need not have an identical sequence. Sequence segments in a 5'-tail that share an identical nucleic acid sequence are repeats.

The terms "5'-end" and "3'-end" interchangeably refer to a nucleotide position on a polynucleotide that is at the 5'- or 3'-terminus (i.e., the 5'- or 3'-terminal base), or 1 or 2 nucleotide base positions from the terminus (i.e., at the (-1) or (-2) position from the 5'- or 3'-terminus) of a nucleic acid or subsequence thereof.

The term "blocking moiety" or "blocking group" refers to a chemical group or moiety attached to the 3'-end of a polynucleotide that prevents the extension of a nucleic acid, e.g., by at least one nucleotide incorporating biocatalyst. Exemplified blocking moieties include substituents at the 2' position of the 3'-end nucleotide base, i.e, a 2'-terminator nucleotide.

A "2'-terminator nucleotide" refers to a nucleotide analog that comprises a blocking group (BG) at the 2'-position of the sugar moiety of the nucleotide. A 2'-terminator nucleotide can be non-extendible by one or more nucleotide incorporating biocatalysts. That is, once a 2'-terminator nucleotide is incorporated into a nucleic acid (e.g., at a 3'-terminal end of the nucleic acid), the blocking group prevents further extension of a nucleic acid by at least one nucleotide incorporating biocatalyst. An exemplary blocking group is a phosphate group. Exemplary 2'-terminator nucleotides include 2'-monophosphate-3'-hydroxyl-5'-triphosphate nucleosides and 2'-monophosphate-3'-hydroxyl-5'-diphosphate nucleosides. 2'-terminator nucleotides are described in detail, for example, in U.S. Patent Publication Nos. 2007/0219361 and 2007/0154914, the disclosures of each of which are hereby incorporated herein by reference.

The term "target nucleic acid" refers to any nucleic acid comprising a subsequence to be detected. The target nucleic acid can be DNA or RNA. A target nucleic acid can come from any source, including genomic DNA, mRNA, cDNA. The target nucleic acid can be naturally occurring or synthetic (e.g., an amplicon, a vector, etc). A target nucleic acid, can be, but need not be purified or isolated. Depending on the nature of a detection assay, the target nucleic acid can be from plant or animal tissue, or taken from a reaction mixture. There is no limit on the length of a target nucleic acid, although a target nucleic acid can be exposed to restriction endonucleases before being subject to detection or identification by the present methods. For the purposes of the present methods, a target nucleic acid is prepared using methods known in the art.

The term "amplification conditions" refers to conditions in an amplification reaction (e.g., a PCR amplification, a RT-PCR amplification) that allow for hybridization of an extendable polynucleotide (e.g., a primer) with a target nucleotide, and the template-dependent extension of the extendable polynucleotide. As used herein, "amplification conditions" or conditions sufficient for amplifying a target nucleic acid are well known in the art. See, e.g., *PCR Primer: A Laboratory Manual*, by Dieffenbach and Dveksler, eds., 2003, Cold Spring Harbor Press; and *PCR Protocols*, Bartlett and Stirling, eds., 2003, Humana Press.

BRIEF DESCRIPTION OF THE DRAWINGS

FIGS. 2A-2G illustrate the successful genotyping of the C allele at a SNP within the H19 gene using methodologies described herein and in Example 1. "GTCTTA" refers to the reverse complement nucleic acid sequence of the repetitive hexamer in the interrogating primer. "Noise" indicates that no discernable signal was detected.

FIGS. 3A-3G illustrate the successful genotyping of the T allele at a SNP within the H19 gene using methodologies described herein and in Example 1. "GCTCTA" refers to the reverse complement nucleic acid sequence of the repetitive hexamer in the interrogating primer. "Noise" indicates that no discernable signal was detected.

FIGS. 4A-4G illustrate the successful concurrent genotyping of the C and T alleles at a SNP within the H19 gene using methodologies described herein and in Example 1, below. "Noise" indicates that no discernable signal was detected.

FIGS. 5A-5D illustrate the successful identification of HIV transcript using 80% or 90% ribonucleotide (here, rATP) and deoxyribonucleotides dU and dC. No signal was obtained from samples without template. See, Example 2. "CCUA" refers to the reverse complement nucleic acid sequence of the repetitive tetramer in the upstream primer (4×CCUA=SEQ ID NO:6). "GUGA" refers to the reverse complement nucleic acid sequence of the repetitive tetramer in the downstream primer (4×GUGA=SEQ ID NO:7). "Noise" indicates that no discernable signal was detected.

FIGS. 6A-6C illustrate the successful identification of HIV transcript using 80% or 90% ribonucleotide (here, rATP) and deoxyribonucleotides dU and 5-Me-dC (4×CmeCmeUA=SEQ ID NO:8; 4×GUGA=SEQ ID NO:7). No signal was obtained from samples without template. See, Example 2. "Noise" indicates that no discernable signal was detected.

FIGS. 7A-7D summarize the results from the test samples illustrated in FIGS. 5A-5D and 6A-6C (4×CmeCmeUA=SEQ ID NO:8; 4×CCUA=SEQ ID NO:6).

DETAILED DESCRIPTION

1. Introduction

Figure 1:
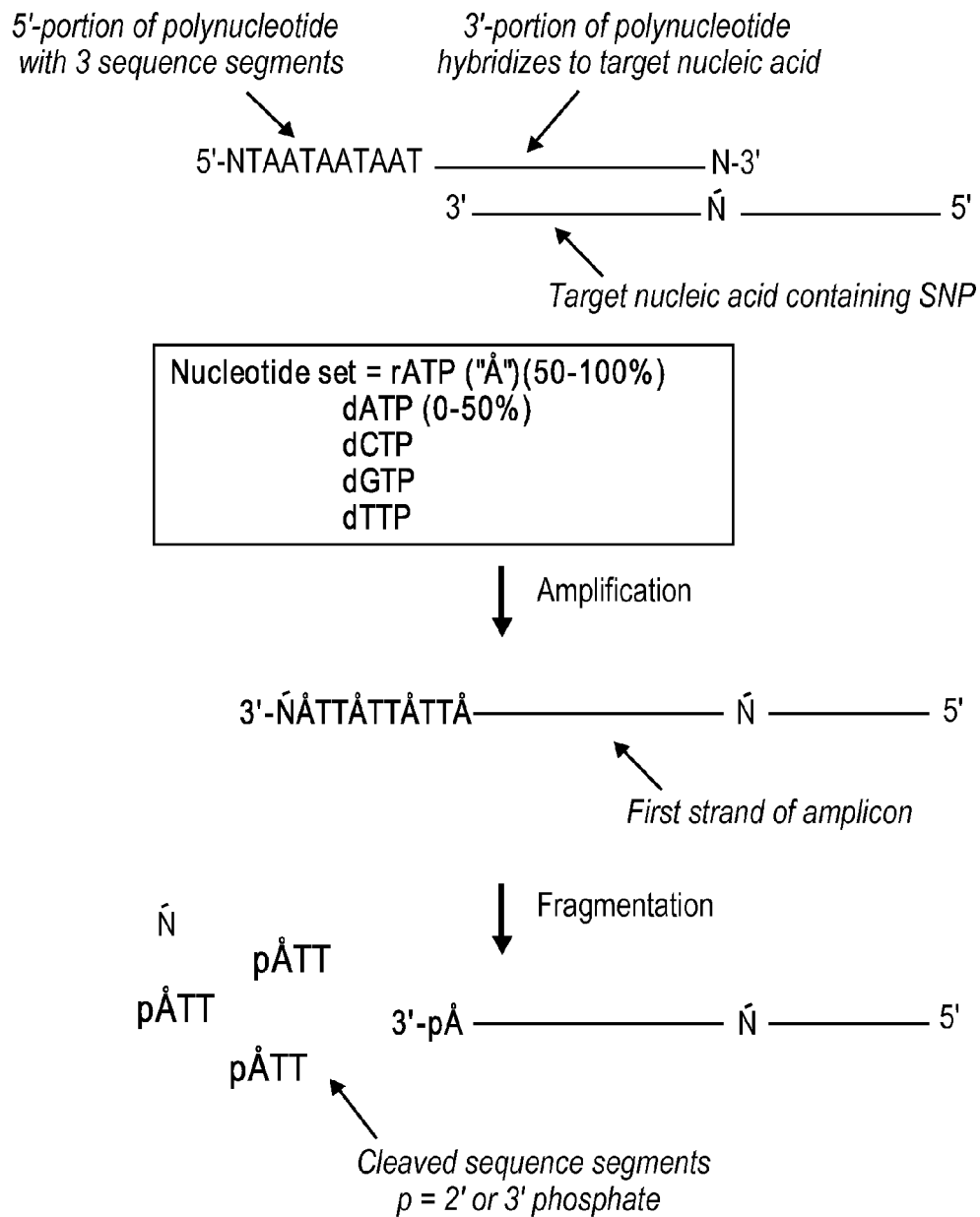
FIG. 1 illustrates a schematic representation of the polynucleotides and methods of the invention. In this exemplary embodiment, the polynucleotide contains a 5'-portion or 5'-tail with 3 identical sequence segments (i.e., "repeats") (5'-NTAATAATAAT-3'; SEQ ID NO: 1). The polynucleotide is being used to detect a polymorphic nucleotide in a target nucleic acid. The nucleotide set can contain from about 50% to 100% of a ribonucleotide that is complementary to the nucleotide that is at the 5'-end position of each sequence segment (e.g., rATP=Å). The ribonucleotides are incorporated into an amplicon strand that is complementary to the polynucleotide. The amplicon is subject to fragmentation, releasing the sequence segments. The mass of the released sequence segments is then detected. Ribonucleotides will also be incorporated into the complementary strand of the target nucleic acid (3'-ÑÅTTÅTTÅTTÅ-5'; SEQ ID NO:2). Therefore, amplified strands of the target nucleic acid will also be subject to cleavage where ribonucleotides are incorporated.

The present invention provides procedures for multiplex detection that require a minimal number of reaction steps and allow for convenient and true multiplexing. The procedures utilize reactions that incorporate ribonucleotide bases (e.g., an amplification reaction in which at least one of the four nucleotides (A, C, G, T) is included, completely or partially, as a ribo base (rNTP)). Primers specific to a target nucleic acid are used. One or both of the primers have a 5'-tail with one, two or more sequence segments of about 3-10, or more, bases, and with a base complementary to the ribo base located at the 5'-end of each sequence segment. The sequence segments can, but need not be of equal mass. The amplification results in inclusion of the primer sequence, including its 5'-portion, into an amplicon (i.e., amplification product). The amplicon will also contain incorporated ribo-bases. For analysis by mass spectrometry, the amplification product is subjected to fragmentation, for example, by exposure to alkali. The base selectively cleaves the DNA backbone immediately 3' to the incorporated ribo bases. Thus, incorporation of the primer sequences, and the sequence segments, in the amplification product allows for detection of the presence of the product by detecting the distinct mass of the sequence segments. The usage of a primer translates into the presence of a product of the mass of the copied and amplified sequence segment.

For multiplexing, primers for multiple target nucleic acids (e.g., different alleles) are tailed with different 5'-portion sequence segments that generate products of distinct mass after cleavage. All neosynthetic DNA contains incorporated ribo base and thus gives rise to fragments when subjected to alkali. To facilitate interpretation, the entire system can be calculated so that generally occurring mass signals from the hybridizing portion of the primer and other nucleic acids are distinct from the masses of the 5'-tail sequence segments, or the complements thereof. The sequence segments in a single tail can be of equal mass and can be identical sequences (i.e., repeats). Reiteration of repeat sequence segments results in clear signals above the signals derived from the sequence(s) of portions of the primers that anneal to or copy a target nucleic acid.

The procedures allow efficient multiplex genotyping for 10 or more samples in a single well with a minimal number of reaction steps. The steps generally require mixing of DNA template and a mastermix. After thermal cycling, a solution of alkali is added and the mass of the fragmented sequence segments is measured, for example, by mass spectrometry. Any known method for mass measurement can be used. When employing mass spectrometry, any kind of mass spectrometer is suitable for analysis.

The primers can optionally contain a removable 3'-end blocking agent (i.e., "hot start") to enable the same thermostable DNA polymerase to effect "hot start," thereby improving specificity and permitting a greater degree of multiplexing.

In one example for performing the present methods, ribo PCR can be carried out with a DNA sample, for each target nucleic acid (e.g., each SNP, each allele), two forward primers and one reverse primer. The forward primers are designed to be specific for one target nucleic acid (e.g., one SNP, one allele), with the 3'-end or pentultimate to 3'-end base specifically complementary to an identifying base on the target nucleic acid. Each forward primer has a specific 5'-tail comprising one, two or more sequence segments of identical mass, wherein the 5'-end base of each sequence segment is complementary to the ribo nucleotide (rNTP) in the PCR amplification mixture. The masses of the sequence segments are designed to be different and distinguishable between different alleles, SNPs, and other detectable target nucleic acids.

To generate sequence segments of distinguishable mass, a the 5'-tail of a primer could contain, for example, about 2-10 sequence segments that are about 3-10 bases in length; or about 4-7 sequence segments about 4-6 bases in length; or about 2-3 sequence segments about 7-8 bases in length.

Ribo-PCR or ribo-amplification is a PCR or amplification reaction with a mix of deoxynucleotides and at least one nucleotide (ribonucleotide or rNTP). An example of this is a PCR mixture comprising dGTP, the ribonucleotide rTTP (i.e., 5-methyl-UTP), dCTP and dATP, and a DNA polymerase that efficiently incorporates and extends ribonucleotides in a suitable buffer. The reaction can be carried out by any extension reaction, including thermal cycling reactions. After thermal cycling, the reaction mixture can be treated with alkali. The alkali can be a strong base, for example, NaOH or KOH. The alkali cleaves the DNA backbone immediately 3' to the incorporated ribo bases and results in the generation of fragments. Presence of the target nucleic acid results in the usage of the forward primer specific for the target nucleic acid and thus the presence of the amplified 5'-tail sequence. The copied and cleaved complement of the tail has a unique mass. This mass is used to determine the presence of a target nucleic acid in the tested sample. The presence of a mass signal corresponding to the cleaved complementary tail sequence is used to identify the presence of the target nucleic acid in the tested sample. For multiplexing, a plurality of different tail sequences are used, each with a base composition that gives rise to a specific mass of the DNA after cleavage.

2. Polynucleotides

The polynucleotides of the invention comprise a 5'-portion or 5'-tail comprised of one, two or more tandem sequence segments and a 3'-portion designed to be sufficiently complementary to anneal to a target nucleic acid to allow for template-based extension of the nucleotide.

a. 5'-Portion

The 5'-portion or 5'-tail comprises one, two or more tandem (i.e., contiguous) sequence segments, each sequence segment containing a unique nucleotide base (i.e., used only once in the segment) that is positioned at the 5'-end of each sequence segment. In some embodiments, each sequence segment in a 5'-portion or 5'-tail is of an equal mass. In some embodiments, each sequence segment in a 5'-portion or 5'-tail has an identical nucleotide sequence. Tandem sequence segments with identical nucleotide sequences are referred to as repeats. The unique nucleotide base can follow the last (2nd, or 3rd, or 4th, etc) tandem sequence segment. For example, the sequence of a 5'-portion or 5'-tail with 3 sequence segments of identical mass, each 4 nucleotides in length could be: 5'-TAGCTAGCTAGCT-3' (SEQ ID NO:3), wherein the nucleotide base "T" is complementary to the ribo base in the reaction mix.

As exemplified above, in some embodiments, the 3'-end nucleotide base of the 5'-portion or 5'-tail is complementary to the ribo base in the reaction mix. Because an alkaline solution cleaves the bond immediately 3' to an incorporated ribo base, including at the 3'-end of the 5'-portion a nucleotide base that is complementary to the ribo base in the reaction mix allows for the release of all sequence segments. What remains at the 3'-end of the cleaved amplicon is an incorporated ribo base with a 2' or 3' phosphate. See, FIG. 1. A nucleotide base that is complementary to the ribo base in the reaction mix positioned at the 3'-end of the 5'-portion is required if the 5'-portion contains only one sequence segment. A nucleotide base that is complementary to the ribo base in the reaction mix positioned at the 3'-end of the 5'-portion also is required if two or more sequence segments are different in mass. However, a nucleotide base that is complementary to the ribo base in the reaction mix positioned at the 3'-end of the 5'-portion is optional if the terminal 5'-nucleotide of target-complementary portion is also the same "unique" nucleotide base or if the 5'-portion contains two or more sequence segments of equal mass.

In some embodiments, an additional nucleotide base is included at the 5'-end of the 5'-portion. The additional 5'-end nucleotide base can be any base. An exemplified 5'-portion with an additional 5'-end nucleotide base could be: 5'-NTAGCTAGCTAGCT-3' (SEQ ID NO:4). Including the additional 5'-end nucleotide base increases the uniformity and accuracy of mass of the released fragments. This is because when the alkaline solution cleaves the bond immediately 3' to an incorporated ribo base a 2' or 3' phosphate moiety remains attached to the ribo base. See, FIG. 1. An additional nucleotide base included at the 5'-end of the 5'-portion finds use when using a nucleotide incorporating biocatalyst that does not carry out template independent extension.

In some embodiments, the sequence segments in a 5'-portion or 5'-tail have identical mass but different sequences. For example, the sequence of a 5'-portion or 5'-tail with 3 sequence segments of identical mass, each 4 nucleotides in length could be: 5'-TAGCTCAGTGCAT-3' (SEQ ID NO:5), wherein the nucleotide base "T" is complementary to the ribo base in the reaction mix.

In some embodiments, the sequence segments in a 5'-portion or 5'-tail can be of different lengths (e.g., 3, 4 and/or 5 nucleotide bases) and different masses, but the whole of the 5'-portion or 5'-tail produces a distinguishable "signature" pattern that can be identified, e.g., by mass spectrometry, when the amplicon is subject to cleavage.

The 5'-portion or 5'-tail can contain from 2 to about 10 sequence segments, or more, as desired, for example, about 2, 3, 4, 5, 6, 7, 8, 9, 10 or more tandem sequence segments. Each sequence segment can be about 3 to about 10 nucleotide bases in length, or longer, for example, about 3, 4, 5, 6, 7, 8, 9, 10 or more nucleotide bases in length. Generally, the longer the sequence segments, the fewer that need be contained in a 5'-tail. Conversely, the shorter the sequence segments, the more that will be contained in a 5'-tail. For example, a 5'-tail could comprise about 2-4 sequence segments that are about 7-8 nucleotide bases in length, or about 4-6 sequence segments that are about 4-6 nucleotide bases in length, or about 5-8 sequence segments that are about 3-5 nucleotide bases in length.

The polynucleotides are useful as primers in target nucleic acid extension and amplification reactions. The unique nucleotide base located at the 5'-end of each 5'-tail sequence segment is complementary to the ribo nucleotide base included in a reaction mixture for the extension or amplification of a target nucleic acid hybridized by the polynucleotides of the invention.

b. 3'-Portion

The 3'-portion of the polynucleotides is designed to have a nucleic acid sequence sufficiently complementary to hybridize to a target nucleic acid sequence and be extended. The 3'-portion is at least 5 nucleotide bases in length, and can be longer, as desired, for example, about 10, 15, 20, 25, 30, 35, 40, 45 or 50 nucleotide bases in length. The 3'-end or (-1) or (-2) to the 3'-end nucleotide base of the 3'-portion can be used to distinguish between specific alleles or SNPs in a target nucleic acid, according to methods known in the art. Exemplary reaction conditions, e.g., for primer extension or thermal cycling include about 50 mM Tricine-KOH, pH 7.5, 100 mM KOAc, 3.0 mM Mg(OAc)$_2$, and 200 μM of each dNTP; annealing or hybridization temperatures can be between about 50° C. and 70° C., for example from about 60-65° C.

In some embodiments, the 3'-end of the 3'-portion optionally has a blocking group or a blocking moiety that reversibly prevents extension of the polynucleotide. Exemplified reversible blocking moieties include substituents attached at the 2' position of the 3'-end nucleotide (i.e., 2'-terminators). In some embodiments, the 2'-terminator moiety is a phosphate or phosphate analog, for example, a methyl amino phosphate.

Generally, the blocking groups (BG) utilized at the 2' position of the sugar moiety can include various embodiments. In some embodiments, for example, BG is a negatively charged group and/or a bulky group. To further illustrate, BG is optionally selected from, e.g., CN, NO$_2$, N$_3$, a halo group, an ether group, an aldehyde group, a carboxylic acid group, an ester group, an amino group, OCH$_3$, OCH$_2$COOH, an O-silylether group, a keto group, an O-lactone group, an O-alkyl group, an O-cyclic alkyl group, an O-alkenyl group, an O-alkynyl group, a carbamate group, an imide group, an amide group, and combinations thereof. More specifically, BG optionally comprises the formula (I):

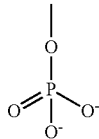

In other embodiments, BG comprises the formula (II):

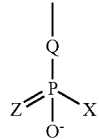

where Q is O, S, or NH; X is H, OH, CH$_3$, BH$_3$, F, or SeH; and Z is O, S, or Se. To further illustrate, BG optionally comprises the formula (III):

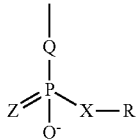

where Q is O, S, or NH; X is O, S, or NH; Z is O, S, or Se; and R is an alkyl group, an alkenyl group, or an alkynyl group. In another exemplary embodiment, BG comprises the formula (IV):

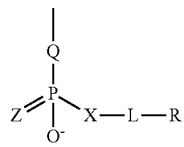

where Q is O, S, or NH; X is O, S, or NH; Z is O, S, or Se; L is —CONH(CH$_2$)$_n$NH—, —CO(CH$_2$)$_n$NH—, or —CONH(CH$_2$CH$_2$O)$_n$CH$_2$CH$_2$NH—; n is an integer greater than 0; and R is NH$_2$, SH, COOH, a quencher moiety, a reporter moiety, biotin, or a affinity moiety.

Exemplary 2'-terminator nucleotides that find use include 2'-monophosphate-3'-hydroxyl-5'-triphosphate nucleosides and 2'-monophosphate-3'-hydroxyl-5'-diphosphate nucleosides. 2'-terminator reversible blocking moieties are described in detail, for example in U.S. Patent Publication Nos. 2007/0219361 and 2007/0154914.

The polynucleotides of the invention can optionally contain non-naturally occurring nucleotide backbone linkages, nucleotide bases and nucleotide base analogs, as described herein. The polynucleotides can be single-stranded or double stranded. In some embodiments, the polynucleotides are single-stranded over their full length. The polynucleotides can, but oftentimes do not, contain any labels, for example, attached fluorophores, radioisotopes, enzymes or other identifiers. The polynucleotides can be isolated, synthesized or recombinant. The polynucleotides, inclusive of the 5'- and 3'-portions, can be any length and are generally about 200 nucleotides or fewer, for example, about 150, 125, 100, 75, 50 or 25, or fewer, nucleotides in length.

3. Methods of Detecting a. Contacting a Target Nucleic Acid with a Polynucleotide of the Invention The first step in performing the methods of detection involves contacting a target nucleic acid with a polynucleotide of the invention, a nucleotide set, and a nucleotide incorporating biocatalytic component.

i. Nucleotide Set

The nucleotide sets used in the present methods contain at least one base in the form of a ribonucleotide base (e.g., A, U, G or C or another ribonucleotide, rNTP). In some embodiments, the nucleotide set contains at least two bases in the form of a ribo nucleotide base. The one or more bases included as a ribonucleotide base can be wholly (e.g., 100% ribonucleotide) or partially (e.g., less than 100% ribonucleotide, e.g., where the remainder of the base is a deoxynucleotide or dNTP) included as a ribonucleotide base in the nucleotide set. In some embodiments, the one or more nucleotide bases are present in a majority portion, i.e., more than 50%, e.g., 60%, 70%, 80%, 85%, 90%, 95%, as a ribonucleotide and in a minority portion (i.e., less than 50%) as a deoxyribonucleotide. The one or more ribonucleotides are included with deoxyribonucleotides to round out a complete nucleotide set (A, T, C and G nucleotides are present).

ii. Biocatalytic Component

The nucleotide incorporating biocatalytic components used in the present methods comprise both deoxyribonucleotide and ribonucleotide incorporating activities. In some embodiments, the same catalytic domain can catalyze both deoxyribonucleotide and ribonucleotide incorporating activities. In some embodiments, the biocatalytic components comprise at least two catalytic domains, one that has deoxyribonucleotide incorporating activity, the other that has ribonucleotide incorporating activity.

Exemplified biocatalyic components suitable for use in the present methods include, without limitation, polymerases that are modified Z05, CS5, CS6 or Taq polymerases. CS5 and CS6 chimeric polymerases are further described in, e.g., U.S. Pat. Application Publication No. 2004/0005599, which is incorporated by reference herein in its entirety. Thermus species Z05 has been published in PCT International Patent Publication No. WO 92/06200, which is incorporated herein by reference in its entirety. Exemplary modified enzymes include, e.g., a G46E E678G CS5 DNA polymerase, a G46E L329A E678G CS5 DNA polymerase, a G46E L329A D640G S671F E678G CS5 DNA polymerase, a G46E L329A T606S D640G S671F E678G CS5 DNA polymerase, a G46E E678G CS6 DNA polymerase, an E615G Taq DNA polymerase, and the like. These modified enzymes comprise mutations that enhance that incorporation of ribonucleotides, and enhance incorporation of 2'-modified analogs of ribonucleotides, and/or that reduce or eliminate 5'-3' exonuclease activity, e.g., relative to an enzyme that lacks one or more of these mutations.

Additional details relating to useful nucleotide incorporating biocatalysts are also provided in, e.g., U.S. patent application Ser. No. 11/873,896 and U.S. Pat. Nos. 5,939, 292; 4,889,818; 5,374,553; 5,420,029; 5,455,170; 5,466, 591; 5,618,711; 5,624,833; 5,674,738; 5,789,224; 5,795, 762; 7,148,049 and 7,179,590, which are each hereby incorporated herein by reference in their entirety for all purposes.

The production of modified enzymes with, e.g., enhanced efficiency for incorporating ribonucleotides and 2'-terminator nucleotides or other desired properties can be accomplished by various processes including, e.g., site-directed mutagenesis, chemical modification, etc. More specifically, site-directed mutagenesis is generally accomplished by site-specific primer-directed mutagenesis. This technique can be conducted using a synthetic oligonucleotide primer complementary to a single-stranded phage DNA to be mutagenized except for a limited mismatch representing the desired mutation. Briefly, the synthetic oligonucleotide is used as a primer to direct synthesis of a strand complementary to the plasmid or phage, and the resulting double-stranded DNA is transformed into a phage-supporting host bacterium. The resulting bacteria can be assayed by, for example, DNA sequence analysis or probe hybridization to identify those plaques carrying the desired mutated gene sequence. To further illustrate, many other approaches to modify nucleic acids, such as "recombinant PCR" methods can also be utilized.

In practicing aspects of the present invention (e.g., producing modified enzymes, performing sequencing reactions, etc.), many conventional techniques in molecular biology and recombinant DNA are optionally utilized. These techniques are well known and are explained in, for example, *Current Protocols in Molecular Biology*, 1997-2007 (F. M. Ausubel ed.), Wiley Interscience; Sambrook et al., 2001, *Molecular Cloning: A Laboratory Manual*, Third Edition, Cold Spring Harbor Laboratory Press, Cold Spring Harbor, N.Y.; Berger and Kimmel, *Guide to Molecular Cloning Techniques Methods in Enzymology* volume 152 Academic Press, Inc., San Diego, Calif. (Berger), *DNA Cloning: A Practical Approach*, Volumes I and II, 1985 (D. N. Glover ed.); *Oligonucleotide Synthesis*, 1984 (M. L. Gait ed.); *Nucleic Acid Hybridization*, 1985, (Hames and Higgins); *Transcription and Translation*, 1984 (Hames and Higgins eds.); *Animal Cell Culture*, 1986 (R. I. Freshney ed.); *Immobilized Cells and Enzymes*, 1986 (IRL Press); Perbal, 1984, *A Practical Guide to Molecular Cloning*; the series, *Methods in Enzymology* (Academic Press, Inc.); *Gene Transfer Vectors for Mammalian Cells*, 1987 (J. H. Miller and M. P. Calos eds., Cold Spring Harbor Laboratory); *Methods in Enzymology* Vol. 154 and Vol. 155 (Wu and Grossman, and Wu, eds., respectively).

iii. Polynucleotides

The 5'-tailed polynucleotides used in the methods are as described above and herein. In some embodiments, a target nucleic acid is contacted with a plurality (e.g., two or more) of 5'-tailed polynucleotides. In some embodiments, each polynucleotide in a plurality is separately identifiable by having a 5'-portion comprising one, two or more sequence segments of a unique mass. In this case, fragmenting the amplicon or complements of each 5'-tailed polynucleotide produces a different mass signal or signature mass profile. In some embodiments, the polynucleotides are contacted to a target nucleic acid as one or more primer pairs. One or both of the polynucleotides in a primer pair can include a 5'-tail comprising tandem sequence segments. Multiple polynucleotides contacting the target nucleic acid as one or more primer pairs can also be provided wherein each primer in the pair comprises a 5'-portion comprising tandem sequence segments of identical mass. In this case, fragmenting the complements of the 5'-portions of each primer in the pair that is used to generate an amplicon produces a single mass signal of greater (e.g., about double) intensity. Alternatively, each primer in a primer pair can contain one sequence segment, the sequence segment in each primer of the pair being of identical mass.

In some embodiments of the methods, the 5'-tailed polynucleotides can comprise one sequence segment of distinct mass to produce a detectable cleavage product.

iv. Target Nucleic Acid

A target nucleic acid can be from any source, e.g., a tissue sample from an animal, a plant, a bacteria or a virus, or can be synthetic, e.g., from a reaction mixture. The target nucleic acid can be, e.g., genomic DNA, a chromosome or chromosomal segment, mRNA, cDNA, a vector (e.g., an expression vector), an expression cassette, a naked DNA or RNA polymer, the product of a polymerase chain reaction (PCR), an oligonucleotide, a probe, a primer, etc. A target nucleic acid can be, e.g., single-stranded, double-stranded, triple-stranded, etc and is not limited to any particular length. Target nucleic acids used in the present methods oftentimes will contain one or more single nucleotide polymorphisms (SNPs), insertions, deletions, substitutions or other distinguishing features. Target nucleic acids are generally provided in a sample.

In some embodiments, the target nucleic acid is contacted (i.e., the methods are performed) with the purpose of distinguishing one or more SNPs. In such an application, at least two different allele-distinguishing 5'-tailed polynucleotides are used that differ in their 3'-portion such that they specifically anneal to a particular allele, and also differ in their 5'-portion such that the one or more sequence segments are of a mass that corresponds to and uniquely identifies the allele bound by the 3'-portion.

In some embodiments, the target nucleic acid is contacted with the purpose of detecting one or more rare mutations in the target nucleic acid. In such an application, one or more polynucleotides having a 3'-portion that specifically anneals to a mutation at a particular position in the target nucleic acid are present (a polynucleotide having a 3'-portion that specifically anneals to the wild-type at the same position can optionally be present in the same or in a separate reaction). Where one mutation in the target nucleic acid sequence is being evaluated, one, two or more different mutation-distinguishing 5'-tailed polynucleotides can be used that differ in their 3'-portion such that they specifically anneal the wild-type or one or more mutation types, and also differ in their 5'-portion such that the one or more sequence segments are of a mass that corresponds to and uniquely identifies the allele bound by the 3'-portion. In applications where two or more mutations in one target nucleic acid are being evaluated, polynucleotides with 3'-portions that specifically detect a mutation at a first position in the target nucleic acid can have 5'-portion sequence segments all of a first mass; polynucleotides with 3'-portions that specifically detect a mutation at a second position in the target nucleic acid can have 5'-portion sequence segments all of a second mass. Alternatively, the masses of the sequence segments in the 5'-portions of the polynucleotides can each be different, operating as unique identifiers.

In some embodiments, e.g., those involving multiplex amplification or extension, the polynucleotides are provided as two or more primer pairs. In the first primer pair, the 5'-portion of each primer in the pair contains sequence segments of a first mass; the second primer pair has 5'-portions of each primer in the pair containing sequence segments of a second mass, detectably distinct from the first mass; the third primer pair has 5'-portions of each primer in the pair containing sequence segments of a third mass, detectably distinct from the mass of the first and second sequence segments; subsequent primer pairs have 5'-portions of each primer in the pair containing sequence segments of a mass detectably distinct from all preceding or other primer pairs. The number of primer pairs and amplification or extension reactions is limited by the availability of free nucleotide bases in the reaction mixture. In some embodiments, a reaction mixture can contain 2, 3, 4, 5, 6, 7, 8, 9, 10, 15, 20 or more primer pairs. This strategy allows for the concurrent detection of multiple target nucleic acids or multiple targets in a single target nucleic acid.

b. Amplifying the Target Nucleic Acid to Produce an Amplicon i. Methods of Amplification The target nucleic acid can be amplified employing one or more of the polynucleotides of the invention using any polynucleotide extension or amplification method known in the art. Amplification using any known variation of a polymerase chain reaction (PCR), including RT-PCR, quantitative PCR, multiplexed and real-time PCR, finds use in the present methods. Amplification also includes isothermal amplification methods and polynucleotide extension methods known in the art. Protocols for carrying out PCR are well known in the art, and are described, for example, in *PCR Primer: A Laboratory Manual*, Dieffenbach and Dveksler, eds., 2003, Cold Spring Harbor Laboratory Press; *A-Z of Quantitative PCR*, Bustin, ed., 2004, International University Line; Edwards, *Real-Time PCR: An Essential Guide*, 2004, Taylor & Francis; *Real Time PCR*, Dorak, ed., 2006, Taylor & Francis; *PCR Protocols: A Guide to Methods and Applications*, Innis, et al., eds., 1990, Academic Press, San Diego; *PCR Strategies*, Innis, et al., eds, 1995, Academic Press, San Diego; and *PCR Applications: Protocols for Functional Genomics*, Innis, et al., eds., 1999, Academic Press, San Diego. The target nucleic acid is amplified or extended for a sufficient amount of time, or for a sufficient number of cycles to produce a detectable amount of amplicon.

As discussed above, one or more target nucleic acids can be amplified or one or more target positions in a single target nucleic acid can be amplified. Because there is essentially no limit on the number of different 5'-portions with sequence segments of a distinguishable mass, the methods are particularly suited to multiplex amplification assays. The one or more polynucleotides used to amplify a target nucleic acid or a specific location within a target nucleic acid can have different 5'-portions with sequence segments of a uniquely identifiable mass. Pairs of polynucleotides used as primer pairs can have 5'-portions with sequence segments of identical mass. In some embodiments, the sequence segments share identical sequences. The multiplex amplification assays can concurrently determine the presence (or absence) of at least 5, 10, 20, 25, 30, 40, 50, 60, 70, 80, 90, 100 or more different target nucleic acids or positions within a target nucleic acid, as desired.

The amplification and polynucleotide extension reactions of the present invention employ a biocatalytic unit (e.g., polymerase) that comprises enzymatic activity to incorporate ribonucleotides into the nucleic acid strand being extended (e.g., "ribo-PCR," or "ribo-amplification," or "ribo-extension"). Exemplified biocatalyic units with ribonucleotide incorporating activities include the G46E CS6R DNA polymerase and the KB17 DNA polymerase, available from Roche Molecular Systems, and described in, for example, Mauger, et al., *Nucleic Acids Research* (2007) 35(8):e62 and Mauger, et al., *Nucleic Acids Research* (2006) 34(3):e18. Additional biocatalytic components that find use are discussed above and herein. See also, U.S. Pat. No. 5,939,292.

ii. Amplicon Produced

Amplifying the target nucleic acid sequence will yield double-stranded amplicons, wherein the strand of the amplicon complementary to the 5'-portion of the polynucleotide will comprise a 3'-portion containing one or more sequence segments, wherein the 3'-end nucleotide base of the sequence segments contain an incorporated ribo-nucleoside monophosphate (rNMP).

c. Cleaving the Amplicon

The sequence segments of the amplicons can be cleaved using any method known in the art. In some embodiments, the amplicons are cleaved at the bond 3' to an incorporated NMP by subjecting the amplicon to an alkaline (i.e., basic solution). The amplicons are exposed to the alkaline solution for a time period and temperature sufficient to effect cleavage of the bonds 3' to an incorporated NMP. Generally, the higher the temperature, the shorter the time period necessary for alkali treatment. For example, the cleaving or fragmenting step can be carried out for about 1.5 hours at 70° C. or for about 8 hours (i.e., overnight) at about 55° C. Alkali treatment temperatures can be as low as refrigerated temperatures (e.g., 4° C.) and as high as near boiling temperatures (e.g., about 95° C.). In some embodiments, the alkaline solution can be any solution with a pH greater than about 8.5, for example, with a pH of at least about 9.0, 9.5, 10.0, 10.5, 11.0, 11.5, 12.0, 12.5, 13.0 or greater. In some embodiments, the alkaline solution will contain at least about 0.2M, 0.3M, 0.5M, 0.8M, 1.0M or more of a basic compound.

The alkaline solution will generally contain at least one strong base. In some embodiments, a weak base can be used, for example, if contained in the alkaline solution at a higher concentration. Generally, the alkaline solutions will contain at least one basic compound with a $pK_b$ of about 5.0 or less, for example a $pK_b$ of about 4.5, 4.0, 3.5, 3.0, 2.5, 2.0, 1.5, 1.0, 0.5 or less. Exemplified basic compounds for use in fragmenting the amplicons at the bonds 3' to an incorporated NMP include, for example, NaOH, KOH, RbOH and $NH_4OH$. Other bases or basic compounds will also find use. See, e.g., Mauger, et al., *Nucleic Acids Research* (2007) 35(8):e62 and Mauger, et al., *Nucleic Acids Research* (2007) 34(3):e18 for procedures of alkaline treatment, the disclosures of both of which are hereby incorporated herein by reference in their entirety for all purposes.

d. Detecting the Amplicon Fragments

The amplicon fragments or cleaved and released sequence segments can be detected using any method known in the art. In some embodiments, the cleaved fragments are detected by identification of mass. The sequence segments can also be detectably labeled before or after cleavage, e.g., with a fluorophore or a radioisotope. Fragments can be labeled at the 5'- or 3'-ends, or on any nucleotide base throughout. Exemplified methods of detection include, without limitation, mass spectrometry, electrophoretic separation, time-resolved fluorescence detection, spin resonance detection and hybridization to a solid phase (e.g., an array) with subsequent detection.

In some embodiments, the cleaved sequence segments released from the amplicon are detected using mass spectrometry. Methods of mass spectrometry are known in the art. Any mass spectrometry technique will find use, including for example, laser desorption-ionization mass spectrometry (e.g., matrix assisted laser desorption-ionization mass spectrometry (MALDI) and surface enhanced laser desorption-ionization mass spectrometry SELDI), gas-phase ion spectrometry, gas-chromatography mass spectrometry, tandem mass spectrometry, and other mass spectrometry techniques. Mass spectrometry methods are well known in the art, and are described for example, in Gross, *Mass Spectrometry: A Textbook*, 2006, Springer Verlag; and Dass, *Fundamentals of Contemporary Mass Spectrometry*, 2007, Wiley Interscience.

The amplicon fragments that are detected can be cleaved sequence segments from the amplicon that are complementary to or amplified from the 5'-portion of the polynucleotide. Of course, it will be appreciated that cleavable sequence segments can be created throughout the length of the amplicon. Under alkaline conditions, the bonds immediately 3' to where ribonucleotides have been incorporated are subject to cleavage. In some embodiments, amplicon fragments can be detected from the amplified target nucleic acid (e.g., from the sequence segments complementary to the 3'-portion of the polynucleotide). As desired, cleaved sequence segments from the 5'-portion and/or the 3'-portion of the polynucleotide, or the complements thereof, can be detected. The signal(s) from the detected amplicon fragments produce a signature of peaks indicative of the target nucleic acid to be identified.

4. Reaction Mixtures

The present invention also provides reaction mixtures involved in the methods of the invention. Any reaction mixtures as described above can be generated. An exemplary reaction mixture comprises, for example, one or more polynucleotides of the invention comprising a 5'-portion or 5'-tail comprised of one, two or more tandem sequence segments and a 3'-portion designed to be sufficiently complementary to anneal to a target nucleic acid; a nucleotide set comprising dNTPs and wherein the majority of at least one base is a ribonucleotide; and a biocatalytic component having ribonucleotide incorporating activity. In some embodiments, the reaction mixtures comprise one or more target nucleic acid sequences. The reaction mixtures of the invention may also comprise amplicons produced by the present methods, the amplicon comprising a 3'-portion having sequence segments complementary to the 5'-portion of the polynucleotides of the invention, wherein the 3'-end nucleotide base of each sequence segment is a nucleoside monophosphate (NMP). A plurality of polynucleotides in the reaction mixtures may be provided in polynucleotide pairs, e.g., as primer pairs. The embodiments of the components in the reaction mixtures are as described above and herein.

In some embodiments, the reaction mixtures comprise two or more primer pairs. In the first primer pair, the 5'-portion of each primer in the pair contains sequence segments of a first mass; the second primer pair has 5'-portions of each primer in the pair containing sequence segments of a second mass, detectably distinct from the first mass; the third primer pair has 5'-portions of each primer in the pair containing sequence segments of a third mass, detectably distinct from the mass of the first and second sequence segments; subsequent primer pairs have 5'-portions of each primer in the pair containing sequence segments of a mass detectably distinct from all preceding or other primer pairs. In some embodiments, a reaction mixture can contain 2, 3, 4, 5, 6, 7, 8, 9, 10, 15, 20 or more primer pairs.

In some embodiments, the reaction mixtures comprise nucleotide sets comprising non-conventional or non-naturally occurring nucleotide bases or labeled nucleotide bases, e.g., with a fluorophore or a radioisotope. Reaction mixtures can also contain buffering components and salts, as needed. In some embodiments, the reaction mixtures comprise an alkaline component, as described above, for example, NaOH or KOH. In accordance with the methods described herein, reaction mixtures containing a high concentration of an alkaline component (e.g., about 0.1 M-0.2 M, or higher) typically have already been subject to amplification.

In some embodiments, the reaction mixtures comprise amplicons produced by the present methods and an alkaline component, as described herein.

5. Kits

The present invention also provides kits for use in the methods of the invention. Typically, the kit is compartmentalized for ease of use and contains containers providing components for performing the present methods, for example, one or more polynucleotides of the invention comprising a 5'-portion or 5'-tail comprised of one, two or more tandem sequence segments and a 3'-portion designed to be sufficiently complementary to anneal to a target nucleic acid; a nucleotide set comprising dNTPs and wherein the majority of at least one base is a ribonucleotide; and a biocatalytic component having ribonucleotide incorporating activity. In some embodiments, the kits comprise one or more target nucleic acid sequences, including control nucleic acid sequences (for positive and/or negative controls). The kits may provide reagents for performing a separate control reaction, including control polynucleotides and control target nucleic acid sequences. A plurality of polynucleotides in the kits may be provided in polynucleotide pairs, e.g., as primer pairs. The embodiments of the components in the kits are as described above and herein.

In some embodiments, the kits comprise two or more primer pairs. In the first primer pair, the 5'-portion of each primer in the pair contains sequence segments of a first mass; the second primer pair has 5'-portions of each primer in the pair containing sequence segments of a second mass, detectably distinct from the first mass; the third primer pair has 5'-portions of each primer in the pair containing sequence segments of a third mass, detectably distinct from the mass of the first and second sequence segments; subsequent primer pairs have 5'-portions of each primer in the pair containing sequence segments of a mass detectably distinct from all preceding or other primer pairs. In some embodiments, a kit can contain 2, 3, 4, 5, 6, 7, 8, 9, 10, 15, 20 or more primer pairs.

One or more additional containers providing additional reagent(s) can also be included. Such additional containers can include any reagents or other elements recognized by the skilled artisan for use in primer extension or amplification procedures in accordance with the methods described above, including reagents for use in, e.g., nucleic acid amplification procedures (e.g., PCR, RT-PCR), DNA sequencing procedures, or DNA labeling procedures. In other, non-mutually exclusive variations, the kit includes one or more containers providing free nucleotides (conventional and/or unconventional). In specific embodiments, the kit includes alpha-phosphorothioate dNTPs, dUTP, dITP, and/or labeled dNTPs such as, e.g., fluorescein- or cyanin-dye family dNTPs. In still other, non-mutually exclusive embodiments, the kit includes one or more containers providing a buffer suitable for a primer extension reaction. In some embodiments, the kits comprise an alkaline component, as described above, for example, NaOH or KOH.

6. Amplicons

The invention also provides amplicons produced by the present methods. PCR amplicons, for example, are usually double-stranded and comprise a strand that is complementary to the polynucleotides of the invention. The amplicons comprise a 3' sequence segment complementary to the 5'-portion of the polynucleotides of the invention,
wherein the 3' sequence segment of the amplicon comprises at least 1, 2 or more sequence segments, wherein the 3'-end nucleotide base of the sequence segments is a nucleoside monophosphate (NMP) having the same base as the NTP in the nucleotide set used to produce the amplicon.

7. Systems

The invention further provides systems for automating the present methods. The systems comprise at least one container or support comprising a composition comprising a polynucleotide or an amplicon or a reaction mixture of the invention; a thermal modulator configured to thermally communicate at one or several temperatures with the composition comprising the polynucleotide or amplicon (e.g., a nucleic acid thermocycling machine; an incubator); at least one reagent transfer mechanism that transfers reagents to or from the container or support; and at least one detector configured to detect mass (e.g., a mass spectrometer, a fluorometer) of the fragmented sequence segments. In some embodiments, the systems comprise at least one controller in operable communication with at least one of the thermal modulator, the reagent transfer mechanism and the detector configure to detect mass.

EXAMPLES

The following examples are provided to illustrate the invention without limitation.

Example 1

Flag-Tag For High Throughput SNP Genotyping

Amplicon containing a SNP in the human H19 gene was prepared for analysis. The target sequence was gtgaggagtgtggagtaggyGCCCAGGCATCGTGCagacagggcgacatcagc (SEQ ID NO:11) (lower case indicates sequences that anneal to the primers, "y" indicates SNP position, C or T). PCR was performed in a total volume of 20 μl, with 2 μl coming from the genomic DNA samples diluted to 10 ng/μl. The PCR amplifications contained the following components: 50 mM Tricine pH 7.5, 100 mM KOAc, 2.75 mM Mg(OAc)$_2$, and 1.6% Storage Buffer, which in turn contained 50% v/v glycerol, 100 mM KCl, 0.1 mM EDTA, 20 mM Tris pH 8.0, 1 mM DTT, and 0.5% Tween 20. Also included in the PCR was 0.2 mM each 5-methyl-dCTP and dGTP, 0.4 mM dUTP, 0.18 mM rATP, 0.02 mM dATP, and 0.1 mM pyrophosphate. The nucleotide base mixture contained 90% rATP and 10% dATP. Enzymes used in the PCR amplifications were 0.02 U/μl Uracil-DNA Glycosylase (UNG) and 20 nM GLTDSE DNA polymerase. See, e.g., PCT Publication Nos. WO 2008/046612 and WO 2009/010251, hereby incorporated herein by reference in their entirety for all purposes. High concentration enzyme stocks (8 U/μl and 5 respectively) were used to minimize glycerol and Tween carry-over.

Primers were added to 0.2 μM each. One primer in common to all reactions had the sequence 5'-GCTGATGTCGCCCTGTC-2'-PO$_4$-U-3' (SEQ ID NO:12). The SNP-interrogating primer was either 5'-CCTAAGACTAAGACTAAGACTC GTGAGGAGTGTGGAGTAGG-2'-PO$_4$-C-3' (SEQ ID NO:13) to detect the H19C allele (see, FIGS. 2A-2G) or -5'-CCTAGAGCTAGAGCTAGAGCTC GTGAGGAGTGTGGAGTAGG-2'-PO$_4$-U-3' (SEQ ID NO:14) to detect the H19T allele (see, FIGS. 3A-3G), or a 50/50 mixture of the two. The portion of the primer corresponding to the target sequence is underlined. These primers include at their 5' ends different repetitive hexamers flanked by T residues: (3×TAAGAC=SEQ ID NO:15) in the primer to detect the H19C allele or (3×TAGAGC=SEQ ID NO:16) in the primer to detect the H19T allele (a single hexamer is bolded in the primer sequences). The repetitive hexamers are not complementary to the genomic targets but, when incorporated into amplicon, result in release of a hexamer "flag-tag" after base digestion.

Thermocycling conditions were: 50° C. for 10 minutes (UNG sterilization); 95° C. for 1 minute (UNG denaturation); then 99 cycles between 92° C. for 15 seconds (denaturation) and 60° C. for 2 minutes (anneal/extension). This was followed by a 5 minute hold at 60° C. Thermocycling was conducted in an ABI 9800.

Six different genomic DNA samples were tested against all three primer pairs, in duplicate. In addition, 4 "no template" controls were run for each primer pair.

Following thermocycling, replicate reactions were pooled. Base was added and the amplicons were heat-treated. In order to desalt the sample, a chelating agent was added and the solutions were centrifuged. Supernatant was applied to the matrix and analyzed in the mass spectrometer. By analyzing the data and noting the appearance of the flag sequences, the genotype of each of the 6 samples at the SNP position was determined. The results are depicted in FIGS. 2A-2G, 3A-3G and 4A-4G.

Example 2

Flag-Tag for High Throughput Screening for Infectious Agents

The application of flag-tag technology to infectious agent screening was tested using RNA transcripts encoding an HIV-derived sequence. Transcript for these experiments was generated by cloning the gag region from HIV strain HXB2 into an expression vector. After linearizing, transcript was made using T7 RNA polymerase. Transcript was then purified over a poly-dT column. The target sequence was catgcagggcctattgcaccaGGCCAGATGAGAGAAC-CAAGGGGaagtgacatagcaggaactactagtaccc ttcagga (SEQ ID NO: 17) (primer sequences are in lower case).

RT-PCR using this transcript was performed in duplicate, with a total volume of 50 μl per reaction. Reactions were performed with and without 10$^6$ copies of transcript per reaction. The reactions contained the following components: 100 mM Tricine pH 7.3, 120 mM KOAc, 1 mM Mn(OAc)$_2$, 0.2 mM dGTP, 0.4 mM dUTP, a mixture of rATP and dATP such that the total was 0.2 mM with either 80% or 90% being rATP, either 0.2 mM dCTP or 0.2 mM 5-methyl-dCTP, and 0.15 mM pyrophosphate. Enzymes used in the reactions were 0.02 U/μl UNG and 25 nM GLDSE DNA polymerase. See, PCT Publication No. WO 2008/046612. High concentration enzyme stocks (2 U/μl and 2.5 μM, respectively)

were used to minimize glycerol and Tween carry-over. Primers were added to 0.2 µM each. The upstream primer had the sequence

5'-ATAGGTAGGTAGGTAGGTCATGCAGGGCCTATTGCACC-2'-PO$_4$-A-3'.

The downstream primer had the sequence 5'-ATCACT-CACTCACTCACT CCTGAAGGGTACTAGTAGTTCCTGCTATGTCACT-2'-PO$_4$-U-3'. The portion of the primer that anneals to the target sequence is underlined. These primers include at their 5' ends different repetitive tetramers flanked by T residues: TCAC and TAGG (a single tetramer is bolded in the primer sequences). The repetitive tetramers are not complementary to the transcript target but, when incorporated into amplicon, result in release of a tetramer "flag-tag" after base digestion. In this example, both primers contain tags. However, as shown in Example 1, it is not necessary to tag both primers to detect amplicon. The use of 5-methyl-dCTP provides for a larger mass difference between tags containing C and U residues. Because dCTP and dUTP differ by only 1 amu, it is difficult to distinguish between them on a mass basis. In contrast dUTP and 5-methyl dCTP are readily distinguishable by determining mass (i.e., differ by more than 1 amu).

Thermocycling conditions were: 50° C. for 2 minutes (UNG sterilization); 60° C. for 60 minutes (reverse transcription step); 93° C. for 1 minute (UNG denaturation); then 60 cycles between 92° C. for 15 seconds (denaturation) and 60° C. for 4 minutes (anneal/extension). Thermocycling was conducted in an ABI 9700.

Amplicon was generated from reactions containing either 80% or 90% rATP and either dCTP or 5-methyl-dCTP. Negative template reactions for these four conditions were also run. Duplicate reactions for all eight conditions were pooled and prepared for analysis. Base was added and the amplicons were heat-treated. In order to desalt the sample, a chelating agent was added and the solutions were centrifuged. Supernatant was applied to the matrix and analyzed in the mass spectrometer. For all samples containing transcript the expected tag sequence was identified by mass spectrometry, but not in the control samples without template. The results are depicted in FIGS. 5A-5D, 6A-6C, 7A-7D.

Example 3

Detection of A/G alleles of SNP R in NOS1_361

Allele-Specific PCR:
Ribo-PCR amplifications in 201 with 1 ng/µl of human genomic DNA, 0.4 µM each primer (Table 1), 0.15 mM sodium pyrophosphate, 100 mM Tricine/KOH at pH 7.3, 100 mM KCOO at pH 7.5, 3 mM Mg(COO)$_2$, 0.2 mM each (rATP, dCTP, dGTP and dTTP) and 0.25 U/µl FP-1 DNA Polymerase (i.e., GLTDSE DNA Polymerase). The thermal cycling profile for the PCR was 4 min at 92° C. followed by 60 cycles of 15 s at 92° C., 4 min at 63° C. This was always concluded at 4° C. 5 µl of PCR was put into a 2% of agarose gel to control the PCR.

Table 1 provides sequences of the primers used in this example. The symbol * indicates a 2'-PO$_4$ containing residue. The symbol (C) indicates a 2'OMe cytidine base. Underline sequence represents the Flag part of the primer and a single heptamer is bolded in the primer sequences.

TABLE 1

| Primer | Sequence | |
|---|---|---|
| Forward 1 | CCTAGAAACTAGAAACTAGAAACTCTG ATGGCTCACCATTGAAAA\* | SEQ ID NO:20 |
| Forward 2 | CCTAAAAACTAAAAACTAAAAACTCTG ATGGCTCACCATTGAAAG\* | SEQ ID NO:21 |
| Reverse | GTCAATGAAGGAAGGTAG(C)A | SEQ ID NO:23 |

Alkali Cleavage:
For alkali cleavage (Table 2) 5.0 µl of 1.2 M sodium hydroxide was added to the remaining 15 µl of the amplification reaction for a final concentration of 0.3 M and incubated at 70° C. for 1.5 hours.

Table 2 shows predicted masses of the fragment of the cleavage of ATP ribo-PCR of the SNP R of NOS1_361. Underline sequence represents the Flag part of the primer and a single heptamer is bolded in the primer sequences.

TABLE 2

| SNP | Sequence | SEQ ID NO: | Mass | Start | End | Sense |
|---|---|---|---|---|---|---|
| | tca | | 940.6 | 28 | 26 | REVERSE |
| | gcca | | 1254.8 | 32 | 29 | REVERSE |
| | ttga | | 1284.8 | 69 | 72 | FORWARD |
| | tggtga | | 1943.2 | 38 | 33 | REVERSE |
| Flag A | | | — | 23 | 17 | REVERSE |
| | | | — | 16 | 10 | REVERSE |
| | gtttcta | | 2182.4 | 9 | 3 | REVERSE |
| Flag G | | | — | 23 | 17 | REVERSE |
| | | | — | 16 | 10 | REVERSE |
| | gttttta | | 2197.4 | 9 | 3 | REVERSE |
| | ccttccttca | 23 | 3009.9 | 59 | 68 | FORWARD |
| | gggggctgcta | 24 | 3509.2 | 48 | 58 | FORWARD |
| G | gtcaatgaaggaaggtagcagccccttctttca | 25 | 10522.8 | 73 | 40 | REVERSE |
| A | gtcaatgaaggaaggtagcagcccctttttca | 26 | 10537.8 | 73 | 40 | REVERSE |

TABLE 2-continued

| SNP | Sequence | SEQ ID NO: | Mass | Start | End | Sense |
|---|---|---|---|---|---|---|
| A | cctagaaactagaaactagaaactctgatggctcaccattgaaaa | 27 | 13919 | 1 | 46 | FORWARD |
| G | cctaaaaactaaaaactaaaaactctgatggctcaccattgaaaga | 28 | 14230.3 | 1 | 46 | FORWARD |

Purification:

Samples were desalted by the addition of cation exchange resin charged with H⁺. 6 mg of resin was added to the reaction with the MassArray® Clean Resin Tool Kit and incubated for 20 minutes at room temperature under agitation. Thereafter, the sample was centrifuged for 2 min at 134×g to sediment the resin.

MALDI-TOF MS:

Trihydroxyacetophenone (THAP) was used as matrix. For preparation 0.5 µl of 0.2 M of 2,4,6 and 2,3,4 THAP in 50% acetonitrile and 0.3 M of ammonium citrate in water in 6/3/2 (v/v) was deposited on an anchor position of MALDI target plate (Anchor Chip™ Target with a spot size of 400 µm, Bruker Daltonik GmbH, Bremen, Germany). After 0.5 µl of the supernatant was added and dried at room temperature.

Figure 8A:
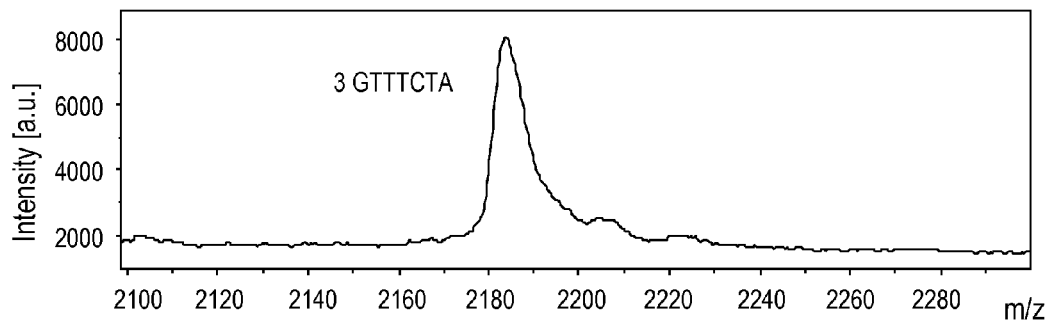
FIGS. 8A-C illustrate a mass spectra of the 7-mer region of the ATP ribo-PCR of the SNP R of NOS1_361. A. Three fragments GTTTCTA (3×GTTTCTA=SEQ ID NO:9) which corresponds to a homozygote A. B. Three fragments GTTTCTA and GTTTTTA (3×GTTTTTA=SEQ ID NO:10) which corresponds to a heterozygote AG. C. Three fragments GTTTTTA which corresponds to a homozygote G.
Figure 8B:
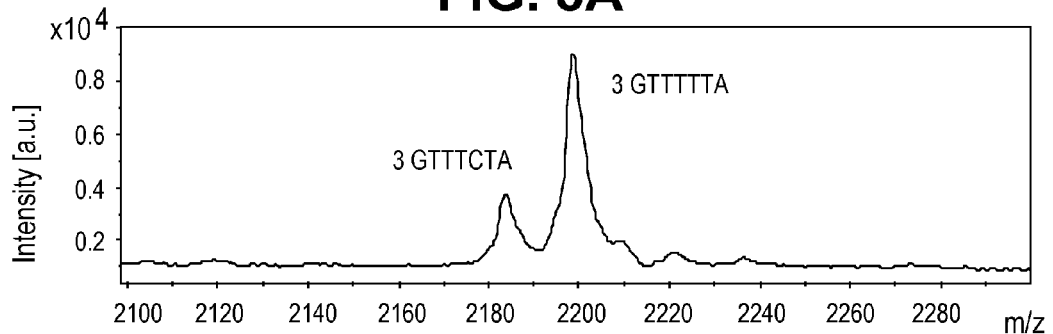
Figure 8C:
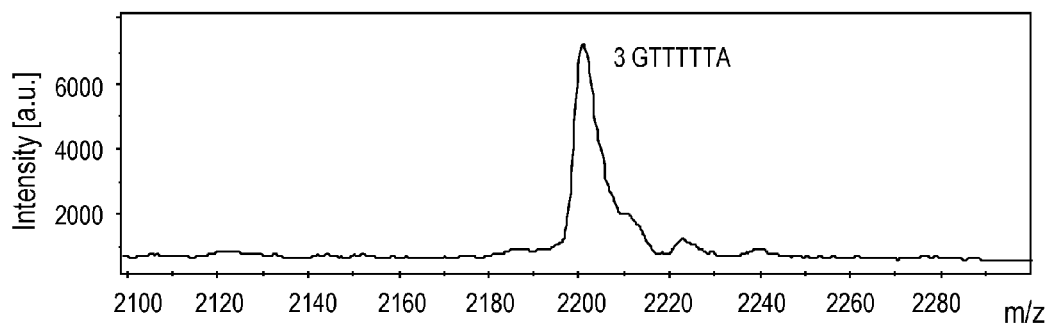

The target was introduced into the MALDI-TOF mass spectrometer (Autoflex, Bruker Daltonik GmbH, Bremen, Germany) for analysis. Mass spectrometry analysis (FIG. 8) was carried out in negative ion mode, with an acceleration voltage of 20 kV using a pulsed ion extraction delay of 100 ns in linear and with external calibration. Each spectrum obtained was the sum of 200 laser shots.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of determining if a sample contains a target nucleic acid, the method comprising:
   (a) contacting the sample with a primer polynucleotide, a nucleotide set and a polymerase to generate an amplification mixture, wherein;
      (i) the primer polynucleotide comprises a 5' portion and a 3' portion, the 5' portion comprising two or more contiguous sequence segments, wherein each sequence segment comprises at least three nucleotide bases, and the 5'-end nucleotide base of each sequence segment is unique within one sequence segment and is the same in each sequence segment;
      (ii) the nucleotide set comprises four different types of nucleotide bases, wherein three nucleotide bases are only in the form of deoxyribonucleotides (dNTPs), and the majority of bases of a fourth type is in the form of a ribonucleotide (rNTP), wherein the base of the ribonucleotide is complementary to the unique 5' nucleotide base of each sequence segment of the primer polynucleotide; and
      (iii) the polymerase comprises deoxyribonucleotide and ribonucleotide incorporating activities;
   (b) submitting the amplification mixture to specific amplification conditions to produce an amplicon, if the target nucleic acid is present, said amplicon comprising two or more contiguous amplicon segments having a known mass, complementary to the two or more contiguous sequence segments in the 5'-portion of the primer polynucleotide, and comprising the rNTP incorporated as the 3'-end nucleotide base of each amplicon segment;
   (c) following said submitting, subjecting the amplification mixture to an alkaline solution not sufficient to degrade DNA but sufficient to cleave the amplicon, if generated, at the site of the incorporated rNTPs, thereby generating a fragment consisting of the amplicon segment; and
   (d) detecting a mass of the fragment, if generated, by mass spectrometry wherein the detected mass indicates amplification of the target nucleic acid sequence, thereby determining if the sample contains the target nucleic acid sequence.

2. The method of claim 1, wherein each 5' portion sequence segment is of equal mass.

3. The method of claim 1, wherein at least 80% of the base of the fourth type is in the form of a ribonucleotide (rNTP).

4. The method of claim 1, wherein the alkaline solution comprises at least one of the following: NaOH, KOH or $NH_4OH$.

5. The method of claim 1, wherein each sequence segment has the same nucleotide sequence.

6. The method of claim 1, comprising contacting the sample with at least two different primer polynucleotides, wherein the 3'-portion of the primer polynucleotides differ only at the 3'-end nucleotide base, wherein the 5' portions of the at least two primer polynucleotides comprise two or more sequence segments, wherein each of the two or more segments of a particular primer polynucleotide are of identical mass, wherein the mass of the sequence segments of the at least two primer polynucleotides is different, and wherein detecting the mass of a fragment consisting of an amplicon segment complementary to the sequence segment indicates which polynucleotide primer, if any, amplified the target nucleic acid.

7. The method of claim 1, wherein the polymerase comprises a single catalytic domain that comprises deoxyribonucleotide and ribonucleotide incorporating activities.

8. The method of claim 1, wherein the polymerase comprises first and second catalytic domains, wherein the first catalytic domain comprises deoxyribonucleotide incorporating activity and the second catalytic domain comprises ribonucleotide incorporating activity.

9. The method of claim 1, wherein the detecting is performed by gas-phase ion mass spectrometry.

10. The method of claim 1, wherein the detecting is performed by laser desorption-ionization mass spectrometry.

11. The method of claim 1, wherein the target nucleic acid is absent from the sample and the detecting does not detect the mass of the fragment.

12. The method of claim 1, wherein the target nucleic acid is a human target nucleic acid and the 3' portion of the primer polynucleotide is complementary to the human target nucleic acid.

* * * * *

SEQUENCE LISTING

```
<160> NUMBER OF SEQ ID NOS: 28

<210> SEQ ID NO 1
<211> LENGTH: 11
<212> TYPE: DNA
<213> ORGANISM: Artificial Sequence
<220> FEATURE:
<223> OTHER INFORMATION: Description of Artificial Sequence:5' portion
      of polynucleotide target nucleic acid with 3 sequence
      segment repeats
<220> FEATURE:
<221> NAME/KEY: modified_base
<222> LOCATION: (1)
<223> OTHER INFORMATION: n = any nucleotide

<400> SEQUENCE: 1
ntaataataa t                                                          11

<210> SEQ ID NO 2
<211> LENGTH: 11
<212> TYPE: DNA
<213> ORGANISM: Artificial Sequence
<220> FEATURE:
<223> OTHER INFORMATION: Description of Combined DNA/RNA Molecule:
      complementary strand to 5' portion of polynucleotide target
      nucleic acid with 3 sequence segment repeats containing
      incorporated ribonucleotides
<220> FEATURE:
<223> OTHER INFORMATION: Description of Artificial Sequence:
      complementary strand to 5' portion of polynucleotide target
      nucleic acid with 3 sequence segment repeats containing
      incorporated ribonucleotides
<220> FEATURE:
<221> NAME/KEY: modified_base
<222> LOCATION: (1)
<223> OTHER INFORMATION: a = adenosine (adenine ribonucleotide)
<220> FEATURE:
<221> NAME/KEY: modified_base
<222> LOCATION: (4)
<223> OTHER INFORMATION: a = adenosine (adenine ribonucleotide)
<220> FEATURE:
<221> NAME/KEY: modified_base
<222> LOCATION: (7)
<223> OTHER INFORMATION: a = adenosine (adenine ribonucleotide)
<220> FEATURE:
```

```
<221> NAME/KEY: modified_base
<222> LOCATION: (10)
<223> OTHER INFORMATION: a = adenosine (adenine ribonucleotide)
<220> FEATURE:
<221> NAME/KEY: modified_base
<222> LOCATION: (11)
<223> OTHER INFORMATION: n = any nucleotide complementary to position 1
      of SEQ ID NO:1

<400> SEQUENCE: 2
attattatta n                                                        11

<210> SEQ ID NO 3
<211> LENGTH: 13
<212> TYPE: DNA
<213> ORGANISM: Artificial Sequence
<220> FEATURE:
<223> OTHER INFORMATION: Description of Artificial Sequence:
      polynucleotide 5'-portion or 5'-tail with identical tandem repeat
      sequence segments

<400> SEQUENCE: 3
tagctagcta gct                                                      13

<210> SEQ ID NO 4
<211> LENGTH: 14
<212> TYPE: DNA
<213> ORGANISM: Artificial Sequence
<220> FEATURE:
<223> OTHER INFORMATION: Description of Artificial Sequence:
      polynucleotide 5'-portion or 5'-tail with identical tandem repeat
      sequence segments and additional nucleotide base
      at 5'-end
<220> FEATURE:
<221> NAME/KEY: modified_base
<222> LOCATION: (1)
<223> OTHER INFORMATION: n = any nucleotide

<400> SEQUENCE: 4
ntagctagct agct                                                     14

<210> SEQ ID NO 5
<211> LENGTH: 13
<212> TYPE: DNA
<213> ORGANISM: Artificial Sequence
<220> FEATURE:
<223> OTHER INFORMATION: Description of Artificial Sequence:
      polynucleotide 5'-portion or 5'-tail with different tandem
      sequence segments

<400> SEQUENCE: 5
tagctcagtg cat                                                      13

<210> SEQ ID NO 6
<211> LENGTH: 16
<212> TYPE: DNA
<213> ORGANISM: Artificial Sequence
<220> FEATURE:
<223> OTHER INFORMATION: Description of Combined DNA/RNA Molecule:
      reverse complement of repetitive tetramer in upstream
      primer
<220> FEATURE:
<223> OTHER INFORMATION: Description of Artificial Sequence:reverse
      complement of repetitive tetramer in upstream
      primer (4 CCUA)
<220> FEATURE:
<221> NAME/KEY: modified_base
<222> LOCATION: (3)
<223> OTHER INFORMATION: n = deoxyuridine (dU)
<220> FEATURE:
<221> NAME/KEY: modified_base
```

<222> LOCATION: (4)
<223> OTHER INFORMATION: a = adenosine (adenine ribonucleotide) or
      deoxyadenosine
<220> FEATURE:
<221> NAME/KEY: modified_base
<222> LOCATION: (7)
<223> OTHER INFORMATION: n = deoxyuridine (dU)
<220> FEATURE:
<221> NAME/KEY: modified_base
<222> LOCATION: (8)
<223> OTHER INFORMATION: a = adenosine (adenine ribonucleotide) or
      deoxyadenosine
<220> FEATURE:
<221> NAME/KEY: modified_base
<222> LOCATION: (11)
<223> OTHER INFORMATION: n = deoxyuridine (dU)
<220> FEATURE:
<221> NAME/KEY: modified_base
<222> LOCATION: (12)
<223> OTHER INFORMATION: a = adenosine (adenine ribonucleotide) or
      deoxyadenosine
<220> FEATURE:
<221> NAME/KEY: modified_base
<222> LOCATION: (15)
<223> OTHER INFORMATION: n = deoxyuridine (dU)
<220> FEATURE:
<221> NAME/KEY: modified_base
<222> LOCATION: (16)
<223> OTHER INFORMATION: a = adenosine (adenine ribonucleotide) or
      deoxyadenosine

<400> SEQUENCE: 6
ccnaccnacc naccna                                                       16

<210> SEQ ID NO 7
<211> LENGTH: 16
<212> TYPE: DNA
<213> ORGANISM: Artificial Sequence
<220> FEATURE:
<223> OTHER INFORMATION: Description of Combined DNA/RNA Molecule:
      reverse complement of repetitive tetramer in downstream
      primer (4 GUGA)
<220> FEATURE:
<223> OTHER INFORMATION: Description of Artificial Sequence:reverse
      complement of repetitive tetramer in downstream
      primer (4 GUGA)
<220> FEATURE:
<221> NAME/KEY: modified_base
<222> LOCATION: (2)
<223> OTHER INFORMATION: n = deoxyuridine (dU)
<220> FEATURE:
<221> NAME/KEY: modified_base
<222> LOCATION: (4)
<223> OTHER INFORMATION: a = adenosine (adenine ribonucleotide) or
      deoxyadenosine
<220> FEATURE:
<221> NAME/KEY: modified_base
<222> LOCATION: (6)
<223> OTHER INFORMATION: n = deoxyuridine (dU)
<220> FEATURE:
<221> NAME/KEY: modified_base
<222> LOCATION: (8)
<223> OTHER INFORMATION: a = adenosine (adenine ribonucleotide) or
      deoxyadenosine
<220> FEATURE:
<221> NAME/KEY: modified_base
<222> LOCATION: (10)
<223> OTHER INFORMATION: n = deoxyuridine (dU)
<220> FEATURE:
<221> NAME/KEY: modified_base
<222> LOCATION: (12)
<223> OTHER INFORMATION: a = adenosine (adenine ribonucleotide) or
      deoxyadenosine
<220> FEATURE:
<221> NAME/KEY: modified_base
<222> LOCATION: (14)
<223> OTHER INFORMATION: n = deoxyuridine (dU)

```
<220> FEATURE:
<221> NAME/KEY: modified_base
<222> LOCATION: (16)
<223> OTHER INFORMATION: a = adenosine (adenine ribonucleotide) or
      deoxyadenosine

<400> SEQUENCE: 7
gngagngagn gagnga                                                    16

<210> SEQ ID NO 8
<211> LENGTH: 16
<212> TYPE: DNA
<213> ORGANISM: Artificial Sequence
<220> FEATURE:
<223> OTHER INFORMATION: Description of Combined DNA/RNA Molecule:
      reverse complement of repetitive tetramer in upstream
      primer (4 CmeCmeUA)
<220> FEATURE:
<223> OTHER INFORMATION: Description of Artificial Sequence:reverse
      complement of repetitive tetramer in upstream
      primer (4 CmeCmeUA)
<220> FEATURE:
<221> NAME/KEY: modified_base
<222> LOCATION: (1)..(2)
<223> OTHER INFORMATION: c = cm
<220> FEATURE:
<221> NAME/KEY: modified_base
<222> LOCATION: (3)
<223> OTHER INFORMATION: n = deoxyuridine (dU)
<220> FEATURE:
<221> NAME/KEY: modified_base
<222> LOCATION: (4)
<223> OTHER INFORMATION: a = adenosine (adenine ribonucleotide) or
      deoxyadenosine
<220> FEATURE:
<221> NAME/KEY: modified_base
<222> LOCATION: (5)..(6)
<223> OTHER INFORMATION: c = cm
<220> FEATURE:
<221> NAME/KEY: modified_base
<222> LOCATION: (7)
<223> OTHER INFORMATION: n = deoxyuridine (dU)
<220> FEATURE:
<221> NAME/KEY: modified_base
<222> LOCATION: (8)
<223> OTHER INFORMATION: a = adenosine (adenine ribonucleotide) or
      deoxyadenosine
<220> FEATURE:
<221> NAME/KEY: modified_base
<222> LOCATION: (9)..(10)
<223> OTHER INFORMATION: c = cm
<220> FEATURE:
<221> NAME/KEY: modified_base
<222> LOCATION: (11)
<223> OTHER INFORMATION: n = deoxyuridine (dU)
<220> FEATURE:
<221> NAME/KEY: modified_base
<222> LOCATION: (12)
<223> OTHER INFORMATION: a = adenosine (adenine ribonucleotide) or
      deoxyadenosine
<220> FEATURE:
<221> NAME/KEY: modified_base
<222> LOCATION: (13)..(14)
<223> OTHER INFORMATION: c = cm
<220> FEATURE:
<221> NAME/KEY: modified_base
<222> LOCATION: (15)
<223> OTHER INFORMATION: n = deoxyuridine (dU)
<220> FEATURE:
<221> NAME/KEY: modified_base
<222> LOCATION: (16)
<223> OTHER INFORMATION: a = adenosine (adenine ribonucleotide) or
      deoxyadenosine

<400> SEQUENCE: 8
ccnaccnacc naccna                                                    16
```

```
<210> SEQ ID NO 9
<211> LENGTH: 21
<212> TYPE: DNA
<213> ORGANISM: Artificial Sequence
<220> FEATURE:
<223> OTHER INFORMATION: Description of Combined DNA/RNA Molecule:
      reverse complement of repetitive heptamer in upstream
      primer (3 GTTTCTA)
<220> FEATURE:
<223> OTHER INFORMATION: Description of Artificial Sequence:reverse
      complement of repetitive heptamer in upstream
      primer (3 GTTTCTA)
<220> FEATURE:
<221> NAME/KEY: modified_base
<222> LOCATION: (7)
<223> OTHER INFORMATION: a = adenosine (adenine ribonucleotide)
<220> FEATURE:
<221> NAME/KEY: modified_base
<222> LOCATION: (14)
<223> OTHER INFORMATION: a = adenosine (adenine ribonucleotide)
<220> FEATURE:
<221> NAME/KEY: modified_base
<222> LOCATION: (21)
<223> OTHER INFORMATION: a = adenosine (adenine ribonucleotide)

<400> SEQUENCE: 9
gtttctagtt tctagtttct a                                               21

<210> SEQ ID NO 10
<211> LENGTH: 21
<212> TYPE: DNA
<213> ORGANISM: Artificial Sequence
<220> FEATURE:
<223> OTHER INFORMATION: Description of Combined DNA/RNA Molecule:
      reverse complement of repetitive heptamer in downstream
      primer (3 GTTTTTA)
<220> FEATURE:
<223> OTHER INFORMATION: Description of Artificial Sequence:reverse
      complement of repetitive heptamer in downstream
      primer (3 GTTTTTA)
<220> FEATURE:
<221> NAME/KEY: modified_base
<222> LOCATION: (7)
<223> OTHER INFORMATION: a = adenosine (adenine ribonucleotide)
<220> FEATURE:
<221> NAME/KEY: modified_base
<222> LOCATION: (14)
<223> OTHER INFORMATION: a = adenosine (adenine ribonucleotide)
<220> FEATURE:
<221> NAME/KEY: modified_base
<222> LOCATION: (21)
<223> OTHER INFORMATION: a = adenosine (adenine ribonucleotide)

<400> SEQUENCE: 10
gtttttagtt tttagttttt a                                               21

<210> SEQ ID NO 11
<211> LENGTH: 53
<212> TYPE: DNA
<213> ORGANISM: Artificial Sequence
<220> FEATURE:
<223> OTHER INFORMATION: Description of Artificial Sequence:human H19
      gene SNP target sequence

<400> SEQUENCE: 11
gtgaggagtg tggagtaggy gcccaggcat cgtgcagaca gggcgacatc agc            53

<210> SEQ ID NO 12
<211> LENGTH: 18
<212> TYPE: DNA
<213> ORGANISM: Artificial Sequence
```

```
<220> FEATURE:
<223> OTHER INFORMATION: Description of Combined DNA/RNA Molecule:PCR
      amplification primer common to all human H19 gene
      SNP reactions
<220> FEATURE:
<223> OTHER INFORMATION: Description of Artificial Sequence:PCR
      amplification primer common to all human H19 gene
      SNP reactions
<220> FEATURE:
<221> NAME/KEY: modified_base
<222> LOCATION: (17)
<223> OTHER INFORMATION: n = c modified by 2'-phosphate

<400> SEQUENCE: 12
gctgatgtcg ccctgtnu                                                   18

<210> SEQ ID NO 13
<211> LENGTH: 42
<212> TYPE: DNA
<213> ORGANISM: Artificial Sequence
<220> FEATURE:
<223> OTHER INFORMATION: Description of Artificial Sequence:human H19
      gene SNP PCR amplification SNP-interrogating primer to
      detect H19C allele
<220> FEATURE:
<221> NAME/KEY: modified_base
<222> LOCATION: (41)
<223> OTHER INFORMATION: n = g modified by 2'-phosphate

<400> SEQUENCE: 13
cctaagacta agactaagac tcgtgaggag tgtggagtag nc                        42

<210> SEQ ID NO 14
<211> LENGTH: 42
<212> TYPE: DNA
<213> ORGANISM: Artificial Sequence
<220> FEATURE:
<223> OTHER INFORMATION: Description of Combined DNA/RNA Molecule:human
      H19 gene SNP PCR amplification SNP-interrogating
      primer to detect H19T allele
<220> FEATURE:
<223> OTHER INFORMATION: Description of Artificial Sequence:human H19
      gene SNP PCR amplification SNP-interrogating primer to
      detect H19T allele
<220> FEATURE:
<221> NAME/KEY: modified_base
<222> LOCATION: (41)
<223> OTHER INFORMATION: n = g modified by 2'-phosphate

<400> SEQUENCE: 14
cctagagcta gagctagagc tcgtgaggag tgtggagtag nu                        42

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence:5'-end
      repetitive hexamers in primer to detect H19C
      allele

<400> SEQUENCE: 15
taagactaag actaagac                                                   18

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence:5'-end
      repetitive hexamers in primer to detect H19T
```

```
            allele

<400> SEQUENCE: 16
tagagctaga gctagagc                                                   18

<210> SEQ ID NO 17
<211> LENGTH: 80
<212> TYPE: DNA
<213> ORGANISM: Artificial Sequence
<220> FEATURE:
<223> OTHER INFORMATION: Description of Artificial Sequence:HIV strain
      HXB2 gag region target sequence

<400> SEQUENCE: 17
catgcagggc ctattgcacc aggccagatg agagaaccaa ggggaagtga catagcagga    60
actactagta cccttcagga                                                 80

<210> SEQ ID NO 18
<211> LENGTH: 39
<212> TYPE: DNA
<213> ORGANISM: Artificial Sequence
<220> FEATURE:
<223> OTHER INFORMATION: Description of Artificial Sequence:HIV strain
      HXB2 gag region RT-PCR upstream primer
<220> FEATURE:
<221> NAME/KEY: modified_base
<222> LOCATION: (38)
<223> OTHER INFORMATION: n = c modified by 2'-phosphate

<400> SEQUENCE: 18
ataggtaggt aggtaggtca tgcagggcct attgcacna                            39

<210> SEQ ID NO 19
<211> LENGTH: 53
<212> TYPE: DNA
<213> ORGANISM: Artificial Sequence
<220> FEATURE:
<223> OTHER INFORMATION: Description of Combined DNA/RNA Molecule:HIV
      strain HXB2 gag region RT-PCR downstream primer
<220> FEATURE:
<223> OTHER INFORMATION: Description of Artificial Sequence:HIV strain
      HXB2 gag region RT-PCR downstream primer
<220> FEATURE:
<221> NAME/KEY: modified_base
<222> LOCATION: (52)
<223> OTHER INFORMATION: n = t modified by 2'-phosphate

<400> SEQUENCE: 19
atcactcact cactcactcc tgaagggtac tagtagttcc tgctatgtca cnu            53

<210> SEQ ID NO 20
<211> LENGTH: 45
<212> TYPE: DNA
<213> ORGANISM: Artificial Sequence
<220> FEATURE:
<223> OTHER INFORMATION: Description of Artificial Sequence:SNP R in
      NOS1_361 ATP ribo-PCR amplification primer Forward 1
<220> FEATURE:
<221> NAME/KEY: modified_base
<222> LOCATION: (45)
<223> OTHER INFORMATION: n = a modified by 2'-phosphate

<400> SEQUENCE: 20
cctagaaact agaaactaga aactctgatg gctcaccatt gaaan                     45

<210> SEQ ID NO 21
<211> LENGTH: 45
<212> TYPE: DNA
```

```
<213> ORGANISM: Artificial Sequence
<220> FEATURE:
<223> OTHER INFORMATION: Description of Artificial Sequence:SNP R in
      NOS1_361 ATP ribo-PCR amplification primer Forward 2
<220> FEATURE:
<221> NAME/KEY: modified_base
<222> LOCATION: (45)
<223> OTHER INFORMATION: n = g modified by 2'-phosphate

<400> SEQUENCE: 21
cctaaaaact aaaaactaaa aactctgatg gctcaccatt gaaan              45

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence:SNP R in
      NOS1_361 ATP ribo-PCR amplification primer Reverse
<220> FEATURE:
<221> NAME/KEY: modified_base
<222> LOCATION: (19)
<223> OTHER INFORMATION: c = cm

<400> SEQUENCE: 22
gtcaatgaag gaaggtagca                                          20

<210> SEQ ID NO 23
<211> LENGTH: 10
<212> TYPE: DNA
<213> ORGANISM: Artificial Sequence
<220> FEATURE:
<223> OTHER INFORMATION: Description of Artificial Sequence:forward
      sense alkali cleavage fragment of ATP ribo-PCR of SNP R
      of NOS1_361

<400> SEQUENCE: 23
ccttccttca                                                     10

<210> SEQ ID NO 24
<211> LENGTH: 11
<212> TYPE: DNA
<213> ORGANISM: Artificial Sequence
<220> FEATURE:
<223> OTHER INFORMATION: Description of Artificial Sequence:forward
      sense alkali cleavage fragment of ATP ribo-PCR of SNP R
      of NOS1_361

<400> SEQUENCE: 24
gggggctgct a                                                   11

<210> SEQ ID NO 25
<211> LENGTH: 34
<212> TYPE: DNA
<213> ORGANISM: Artificial Sequence
<220> FEATURE:
<223> OTHER INFORMATION: Description of Artificial Sequence:reverse
      sense alkali cleavage fragment of ATP ribo-PCR of SNP R
      of NOS1_361

<400> SEQUENCE: 25
gtcaatgaag gaaggtagca gccccttct ttca                          34

<210> SEQ ID NO 26
<211> LENGTH: 34
<212> TYPE: DNA
<213> ORGANISM: Artificial Sequence
<220> FEATURE:
<223> OTHER INFORMATION: Description of Artificial Sequence:reverse
```

-continued

```
      sense alkali cleavage fragment of ATP ribo-PCR of SNP R
      of NOS1_361

<400> SEQUENCE: 26
gtcaatgaag gaaggtagca gcccccttttt ttca                              34

<210> SEQ ID NO 27
<211> LENGTH: 45
<212> TYPE: DNA
<213> ORGANISM: Artificial Sequence
<220> FEATURE:
<223> OTHER INFORMATION: Description of Artificial Sequence:SNP R in
      NOS1_361 ATP ribo-PCR amplification primer forward
      sense

<400> SEQUENCE: 27
cctagaaact agaaactaga aactctgatg gctcaccatt gaaaa                   45

<210> SEQ ID NO 28
<211> LENGTH: 46
<212> TYPE: DNA
<213> ORGANISM: Artificial Sequence
<220> FEATURE:
<223> OTHER INFORMATION: Description of Artificial Sequence:SNP R in
      NOS1_361 ATP ribo-PCR amplification primer forward
      sense

<400> SEQUENCE: 28
cctaaaaact aaaaactaaa aactctgatg gctcaccatt gaaaga                  46
```